US006306889B1

(12) United States Patent
Li et al.

(10) Patent No.: US 6,306,889 B1
(45) Date of Patent: *Oct. 23, 2001

(54) COMPOUNDS, METHODS AND PHARMACEUTICAL COMPOSITIONS FOR TREATING NEURAL OR CARDIOVASCULAR TISSUE DAMAGE

(75) Inventors: Jia-He Li, Cockeysville; Jie Zhang, Ellicott City; Paul F. Jackson, Bel Air; Keith M. Maclin, Baltimore, all of MD (US)

(73) Assignee: Guilford Pharmaceuticals Inc., Baltimore, MD (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/047,502

(22) Filed: Mar. 25, 1998

Related U.S. Application Data

(63) Continuation-in-part of application No. 08/922,548, filed on Sep. 3, 1997.

(51) Int. Cl.⁷ ..................... A61K 31/407; C07D 491/052
(52) U.S. Cl. ............................................. 514/410; 548/421
(58) Field of Search ................................... 514/288, 410; 546/68, 69; 549/384; 548/421

(56) References Cited

U.S. PATENT DOCUMENTS

| | | | |
|---|---|---|---|
| Re. 31,617 | 6/1984 | Beverung, Jr. et al. | 260/285.5 |
| Re. 36,397 | 11/1999 | Zhang et al. | 514/309 |
| 932,920 | 8/1909 | Kacer et al. | 260/250 |
| 1,001,325 | 8/1911 | Ullman et al. | 260/250 |
| 1,253,252 | 1/1918 | Kardos et al. | 546/76 |
| 1,880,441 | 10/1932 | Heidenrich et al. | |
| 1,895,105 | 1/1933 | Rath et al. | 260/288 |
| 2,467,692 | 4/1949 | Petrow | 260/288 |
| 2,593,798 | 4/1952 | Robinson | 260/286 |
| 2,612,503 | 9/1952 | Ullyot | 260/288 |
| 2,638,472 | 5/1953 | Grewe | 260/286 |
| 2,666,059 | 1/1954 | Davis et al. | 260/288 |
| 2,700,040 | 1/1955 | Ullyot | 260/286 |
| 2,892,841 | 6/1959 | Rudner | 260/288 |
| 2,992,220 | 7/1961 | Irving et al. | 260/250 |
| 3,247,212 | 4/1966 | Johnson | 260/287 |
| 3,291,801 | 12/1966 | Montgomery | 260/289 |
| 3,300,499 | 1/1967 | Lesher | 260/288 |
| 3,403,157 | 9/1968 | Humber et al. | 260/288 |
| 3,507,872 | 4/1970 | Hegar | 260/280 |
| 3,534,038 | 10/1970 | Machatzke et al. | 260/256.4 |
| 3,557,119 | 1/1971 | Humber | 260/287 |
| 3,573,304 | 3/1971 | Eberle et al. | 260/250 |
| 3,700,673 | 10/1972 | Watson | 260/287 |
| 3,719,684 | 3/1973 | Unger et al. | 206/294.8 |
| 3,759,924 | 9/1973 | Jeanmart et al. | 260/286 R |
| 3,830,816 | 8/1974 | Gittos et al. | 260/286 R |
| 3,838,134 | 9/1974 | Glauthier | 260/286 A |
| 3,899,529 | 8/1975 | Witzel | 260/517 |
| 3,900,477 | 8/1975 | Philipp et al | 260/288 |
| 3,904,671 | 9/1975 | Minatoya | 260/473 R |
| 3,932,643 | 1/1976 | Gauthier | 424/258 |
| 3,950,343 | 4/1976 | Philipp et al. | 260/288 |
| 3,978,066 | 8/1976 | Philipp et al. | 260/288 |
| 3,991,064 | 11/1976 | Brown et al. | 260/288 |
| 4,031,097 | 6/1977 | Bach et al. | 260/285.5 |
| 4,082,741 | 4/1978 | Hunger et al. | 260/154 |
| 4,169,897 | 10/1979 | Meyer et al. | 424/330 |
| 4,218,453 | 8/1980 | Hannart | 424/256 |
| 4,309,543 | 1/1982 | Keeley | 546/76 |
| 4,382,943 | 5/1983 | Winter et al. | 424/267 |
| 4,472,401 | 9/1984 | Kennewell et al. | 424/251 |
| 4,594,415 | 6/1986 | Robins et al. | 536/27 |
| 4,639,454 | 1/1987 | Hesson | 514/259 |
| 4,740,518 | 4/1988 | Pruett et al. | 528/289 |
| 4,742,171 | 5/1988 | Martin et al. | 546/81 |
| 4,902,695 | 2/1990 | Ornstein | 514/307 |
| 4,902,798 | 2/1990 | Nakamatsu et al. | 546/76 |
| 4,925,698 | 5/1990 | Sestanj et al. | 560/21 |
| 5,032,617 | 7/1991 | Lee et al. | 514/617 |

(List continued on next page.)

FOREIGN PATENT DOCUMENTS

| | | |
|---|---|---|
| 562948 | 12/1957 | (BE) . |
| 628255 | 2/1963 | (BE) . |
| 1000701 | 11/1976 | (CA) . |
| 1274339 | 9/1990 | (CA) . |
| 1278141 | 12/1990 | (CA) . |
| 463 778 | 10/1968 | (CH) . |
| 282711 | 3/1915 | (DE) . |
| 2827111 | 3/1915 | (DE) . |
| 963 184 | 5/1957 | (DE) . |
| 2111910 | 10/1971 | (DE) . |
| 2429515 | 6/1973 | (DE) . |

(List continued on next page.)

OTHER PUBLICATIONS

Chemical Abstract vol. 84:4857 1976 Cookson.

Chemical Abstract vol. 86:171282 1977 Humber.

Chemical Abstract vol. 87:152015 1977 Houlihan.

Chemical Abstract vol. 97:38635 1982 Krepelka.

Chemical Abstract vol. 100:139054 1984 Oleinik.

Chemical Abstract vol. 124:131261 1996 Richter.

(List continued on next page.)

*Primary Examiner*—Richard L. Raymond
(74) *Attorney, Agent, or Firm*—Nixon & Vanderhye PC

(57) ABSTRACT

This invention relates to compounds, pharmaceutical compositions, and methods for the treatment or prevention of neural or cardiovascular tissue damage related to cerebral ischemia and reperfusion injury in an animal by administering Poly(ADP-ribose) polymerase ("PARP") inhibitors.

10 Claims, No Drawings

U.S. PATENT DOCUMENTS

| | | | |
|---|---|---|---|
| 5,041,653 | 8/1991 | Lee et al. | 564/74 |
| 5,077,035 | 12/1991 | Wieland et al. | 424/1.1 |
| 5,215,738 | 6/1993 | Lee et al. | 424/10 |
| 5,262,564 | 11/1993 | Schohe et al. | 562/430 |
| 5,274,097 | 12/1993 | Schohe et al. | 546/208 |
| 5,338,851 | 8/1994 | Huff et al. | 546/141 |
| 5,391,376 | 2/1995 | Long, Jr. et al. | 424/450 |
| 5,395,835 | 3/1995 | Glase et al. | 514/254 |
| 5,414,001 | 5/1995 | Ireland et al. | 514/296 |
| 5,420,136 | 5/1995 | Lewis et al. | 514/296 |
| 5,434,188 | 7/1995 | Boschelli et al. | 514/617 |
| 5,464,871 | 11/1995 | Kun et al. | 514/617 |
| 5,473,074 | 12/1995 | Kun et al. | 546/141 |
| 5,480,631 | 1/1996 | De Paulis et al. | 424/185 |
| 5,482,975 | 6/1996 | Kun et al. | 514/619 |
| 5,516,941 | 5/1996 | Kun et al. | 564/166 |
| 5,589,483 | 12/1996 | West | 514/310 |
| 5,618,813 | 4/1997 | Chu et al. | 514/233.2 |
| 5,633,282 | 5/1997 | Collins et al. | 514/622 |
| 5,635,506 | 6/1997 | Alberts et al. | 514/232.8 |
| 5,652,260 | 7/1997 | Kun et al. | 514/457 |
| 5,652,367 | 7/1997 | Kun et al. | 546/141 |
| 5,656,638 | 8/1997 | Gaeta et al. | 514/301 |
| 5,659,082 | 8/1997 | Flitter et al. | 564/166 |
| 5,665,710 | 9/1997 | Rahman et al. | 514/44 |
| 5,670,518 | 9/1997 | Kun et al. | 514/309 |
| 5,703,089 | 12/1997 | Braña et al. | 514/284 |
| 5,703,116 | 12/1997 | Gaeta et al. | 514/493 |
| 5,719,151 | 2/1998 | Shall et al. | 514/248 |
| 5,753,674 | 5/1998 | Kun et al. | 514/309 |
| 5,756,510 | 5/1998 | Griffin et al. | 514/261 |
| 5,760,062 | 6/1998 | Gaeta et al. | 514/544 |
| 5,767,135 | 6/1998 | Fernandez-Pol | 514/354 |
| 6,121,278 | 9/2000 | Li et al. | 514/292 |

FOREIGN PATENT DOCUMENTS

| | | |
|---|---|---|
| 26 50 226 | 5/1978 | (DE) . |
| 33 32 633 | 4/1985 | (DE) . |
| 0 005 232 | 6/1982 | (EP) . |
| 0 126 684 B1 | 11/1984 | (EP) . |
| 0 212 959 B1 | 3/1986 | (EP) . |
| 0 197 718 B1 | 10/1986 | (EP) . |
| 355 750 | 2/1990 | (EP) . |
| 0 393 926 | 10/1990 | (EP) . |
| 393926 | 10/1990 | (EP) . |
| 0 219 208 B1 | 6/1992 | (EP) . |
| 0 539 805 | 5/1993 | (EP) . |
| 0 638 309 A1 | 2/1995 | (EP) . |
| 0676 201 | 10/1995 | (EP) . |
| 1 199 252 | 12/1957 | (FR) . |
| 7 723 M | 11/1971 | (FR) . |
| 2 205 333 | 7/1974 | (FR) . |
| 2 305 182 | 11/1976 | (FR) . |
| 810108 | 3/1959 | (GB) . |
| 838994 | 6/1960 | (GB) . |
| 1263044 | 2/1972 | (GB) . |
| 1379111 | 1/1975 | (GB) . |
| 1474775 | 5/1977 | (GB) . |
| 1545767 | 5/1979 | (GB) . |
| 032 05402 A2 | 9/1991 | (JP) . |
| 3-205402 | 9/1991 | (JP) . |
| 040 13684 A2 | 1/1992 | (JP) . |
| 4-13684 | 3/1992 | (JP) . |
| 042 75223 A2 | 9/1992 | (JP) . |
| 042 75296 A2 | 9/1992 | (JP) . |
| 4-275223 | 9/1992 | (JP) . |
| 4-275296 | 9/1992 | (JP) . |
| WO 96/33268 | 10/1996 | (SO) . |
| WO 90/07502 | 7/1990 | (WO) . |
| WO 92/00218 | 1/1992 | (WO) . |
| WO 92/05770 | 4/1992 | (WO) . |
| WO 92/15286 | 9/1992 | (WO) . |
| WO 93/05096 | 3/1993 | (WO) . |
| WO 93/18748 | 9/1993 | (WO) . |
| WO 95/04720 | 2/1995 | (WO) . |
| WO 95/24379 | 9/1995 | (WO) . |
| WO 95/29895 | 11/1995 | (WO) . |
| WO 95/30409 | 11/1995 | (WO) . |
| WO 96/28167 | 9/1996 | (WO) . |
| WO 97/30054 | 8/1997 | (WO) . |
| WO 98/27975 | 7/1998 | (WO) . |
| WO 99/11622 | 3/1999 | (WO) . |
| WO 99/11623 | 3/1999 | (WO) . |
| WO 99/11624 | 3/1999 | (WO) . |
| WO 99/11628 | 3/1999 | (WO) . |
| WO 99/11644 | 3/1999 | (WO) . |
| WO 99/11645 | 3/1999 | (WO) . |
| WO 99/11649 | 3/1999 | (WO) . |
| WO 99/59975 | 11/1999 | (WO) . |
| Wo 99/59973 | 11/1999 | (WO) . |
| WO 00/39070 | 7/2000 | (WO) . |
| WO 00/39104 | 7/2000 | (WO) . |

OTHER PUBLICATIONS

Chemical Abstract vol. 52:5846 1958 Schmidt–Nickels.

Chemical Abstract vol. 54:22647 1960 Campbell.

Chemical Abstract vol. 58:7884 1963 Sieglitz.

Chemical Abstract vol. 59:10037 1963 Dokunikhin et al.

Chemical Abstract vol. 61:9493 1964 Dokunikhin et al.

Chemical Abstract vol. 63:7006 1965 Perrin.

Chemical Abstract vol. 64:3526h 1966 Crossland.

Chemical Abstract vol. 69:87767 1968 Hofer.

Chemical Abstract vol. 70:115926 1969 Hofer.

Chemical Abstract vol. 74:111797 1971 Mavoungou–Gomes.

Chemical Abstract vol. 75:98422 1971 Campbell.

Chemical Abstract vol. 76:14566 1972 Rodway.

Chemical Abstract vol. 76:85774 1972 Mavoungou–Gomes.

Chemical Abstract vol. 77:61927 1972 Zinchenko.

Chemical Abstract vol. 81:37417 1974 Baddar.

Chemical Abstract vol. 82:170471 1975 Mavoungou–Gomes.

Chemical Abstract vol. 82:171011 1975 Rodway.

Chemical Abstract vol. 83:27978 1975 Baddar.

Chemical Abstract vol. 84:3986 1976 Zaitsev.

Chemical Abstract vol. 84:42754 1976 Zaitsev.

Chemical Abstract vol. 95:168911 1981 Houlihan.

Chemical Abstract vol. 90:38734 1979 Mavoungou–Gomes.

Chemical Abstract vol. 92:146482 1980 Rokach.

Chemical Abstract vol. 92:198336 1980 Cabares.

Chemical Abstract vol. 93:26178 1980 Gome.

R. J. Griffin et al., Abstract of "The role of poly(ADP–ribose) polymerase as resistance–modifying agents in cancer therapy", Biochimie vol. 77 No. 6, pp. 408–422 (1995).

A. L. Harris, Abstract of "DNA repair: relationship to drug and radiation resistance, metastasis and growth fators", Int. J. Radiat. Biol. Relat. Stud. Phys. Chem. Med. vol. 48 No. 5, pp. 675–690 (1985).

Tim T. Lam, "The effect of 3–aminobenzamide, an inhibitor of poly–ADP–ribose polymerase, on ischemia/reperfusion damage in rat retina", Res. Comm. Mol. Pathol. Pharmacol. vol. 95 No. 3, pp. 241–252 (Mar. 1997).

Jianren Mao et al., "The inhibition of nitric oxide–activated poly(ADP–ribose) synthetase attenuates transsynaptic alteration of spinal cord dorsal horn neurons and neuropathic pain in the rat", Pain vol. 72, pp. 355–366 (1997).

G. P. Paaphorst & E.I. Azzam, Full citation of "Poly–ADP–ribose synthetase inibitors increase radiation and thermal sensitivity but do not affect thermotolerance", Radiat. Res. vol. 116 No. 3, pp. 442–452 (1988).

Armin Rug et al., "Structure of the catalytic fragment of poly(ADP–ribose) polymerase from chicken", Proc. Natl. Acad. Sci. USA vol. 93, pp. 7481–7485 (Jul. 1996).

Geoffrey N. Sklar et al., "Combined antitumor effect of suramin plus irradiation in human prostate cancer cells: the role of apoptosis", J. Urol. vol. 150, pp. 1526–1532 (Nov. 1993).

Léon Van Gool et al., "Overexpression of human poly(ADP–ribose) polymerase in transfected hamster cells leads to increased poly(ADP–ribosyl)ation and cellular sensitization to γ irradiation", Eur. J. Biochem. vol. 244, pp. 15–20 (1997).

Homayoun Vaziri et al., "ATM–dependent telomere loss in aging human dipoloid fibroblasts and DNA damage lead to the post–translational activation of p53 protein involving poly(ADP–ribose) polymerase", The EMBO Journal vol. 16 No. 19, pp. 6018–6033 (1997).

D. Weltin et al., Abstract of "Effect of 6(5H–phenanthridinone, a poly (ADP–ribose)polymerase inhibitor, and ionizing radiation on the growth of cultured lymphoma cells", Int. J. Radiat. Biol. vol. 72 No. 6, pp. 685–692 (Dec. 1997).

Bauer et al., "Modification of Growth Related Enzymatic Pathways and Apparent Loss of Tumorigenicity of a ras–transformed Bovine Endothelial Cell Line by Treatment with 5–Iodo–6–amino–1,2–benzopyrone (INH$_2$BP)", Intl. J. Oncol., 8:239–52 (1996).

Cosi et al., "Poly(ADP–Ribose) Polymerase (PARP) Revisited. A New Role for an Old Enzyme: PARP Involvement in Neurodegeneration and PARP Inhibitors as Possible Neuroprotective Agents", Ann. N. Y. Acad. Sci., 825:366–79 (1997).

Cosi et al., "Poly(ADP–Ribose) Polymerase Inhibitors Protect Against MPTP–induced Depletions of Striatal Dopamine and Cortical Noradrenaline in C57B1/6 Mice", Brain Res., 729:264–69 (1996).

Cristovao et al., "Effect of a Poly(ADP–Ribose) Polymerase Inhibitor on DNA Breakage and Cytotoxicity Induced by Hydrogen Peroxide and γ–Radiation", Terato., Carcino., and Muta., 16:219–27 (1996).

Cuzzocrea, "Role of Peroxynitrite and Activation of Poly-(ADP–Ribose) Synthetase in the Vascular Failure Induced by Zymosan–activated Plasma", Brit. J. Pharm., 122:493–503 (1997).

Endres et al., "Ischemic Brain Injury is Mediated by the Activation of Poly(ADP–Ribose) Polymerase", J. Cerebral Flood Flow Metabol., 17(11):1143–51 (1997).

Heller et al., "Inactivation of the Poly(ADP–Ribose) Polymerase Gene Affects Oxygen Radical and Nitric Oxide Toxicity in Islet Cells", J. Biol. Chem., 270:11176–80 (1995).

Hughes et al., "Induction of T Helper Cell Hyporesponsiveness in an Experimental Model of Autoimmunity by Using Nonmitogenic Anti–CD3 Monoclonal Antibody", J. Immuno., 153:3319–25 (1994).

Salzman et al., "Role of Peroxynitrite and Poly(ADP–Ribose) Synthase Activation Experimental Colitis", Japanese J. Pharm., 75, Supp. I:15 (1997).

Southan et al., "Spontaneous Rearrangement of Aminoalkylisothioureas into Mercaptoalkylguanidines, a Novel Class of Nitric Oxide Synthase Inhibitors with Selectivity Towards the Inducible Isoform", Br. J. Pharm., 117:619–32 (1996).

Szabó et al., "Mercaptoethylguanidine and Guanidine Inhibitors of Nitric Oxide Synthase React with Peroxynitrite and Protect Against Peroxynitrite–induced Oxidative Damage", J. Biol. Chem., 272:9030–36 (1997).

Szabó et al., "Protective Effects of an Inhibitor of Poly(ADP–Ribose) Synthetase in Collagen–Induced Arthritis," Japanese J. Pharm., 75, Supp. I:102 (1997).

Szabó et al., "DNA Strand Breakage, Activation of Poly-(ADP–Ribose) Synthetase, and Cellular Energy Depletion are Involved in the Cytotoxicity in Macrophages and Smooth Muscle Cells Exposed to Peroxynitrite", Proc. Natl. Acad. Sci. USA, 93:1753–58 (1996).

Wallis et al., Traumatic Neuroprotection with Inhibitors of Nitric Oxide and ADP–Ribosylation, Brain Res., 710:169–77 (1996).

Weltin et al., "Effect of 6($5_H$)–Phenanthridinone, an Inhibitor of Poly(ADP–ribose) Polymerase, on Cultured Tumor Cells", Oncol. Res., 6:399–403 (1994).

Zingarelli et al., "Protective Effects of Nicotinamide Against Nitric Oxide–Mediated Delayed Vascular Failure in Endotoxic Shock: Potential Involvement of PolyADP Ribosyl Synthetase", Shock, 5:258–64 (1996).

Langlois et al., "Synthesis of Quinazoline–2,4–dione nad Naphthalimide Derivatives as New 5–HT$_3$ Receptor Antagonists", Eur. J. Med. Chem., 29, 925–40 (1994).

Dokunichin, Beilstein Handbook of Organic Chem., Reg. No. 618403, 1988.

Dokunichin, Beilstein Handbook of Organic Chem., Reg. No. 827161, 1988.

Dokunichin, Beilstein Handbook of Organic Chem., Reg. No. 821484, 1988.

Dokunichin, Beilstein Handbook of Organic Chem., Reg. No. 619108, 1988.

Dokunichin, Beilstein Handbook of Organic Chem., Reg. No. 6557772, 1988.

Dokunichin, Belstein Handbook of Organi Chem., Reg. No. 653888, 1988.

Oleinik, Beilstein Handbook of Organic Chem., Reg. No. 4483194, 1991.

Oleinik, Beilstein Handbook of Organic Chem., Reg. No. 4494786, 1991.

Sielitz, Beilstein Handbook of Organic Chem., Reg. No. 807993, 1988.

Dokunichin, Beilstein Handbook of Organic Chem., Reg. No. 746893, 1988.

Gomes, Beilstein Handbook of Organic Chem., Reg. No. 656117, 1988.

Rokach, Beilstein Handbook of Organic Chem., Reg. No. 1571164, 1988.

Humber et al., Beilstein Handbook of Organic Chem., Reg. No. 154605, 1988.

Mavoungou Gomes, Beilstein Handbook of Organic Chem., Reg. No. 670954, 1988.

Mavoungou, Gomes, Beilstein Handbook of Organic Chem., Reg. No. 670954, 1988.

Dokunichin, Beilstein Handbook of Organic Chem., Reg. No. 649696, 1988.

Dokunichin, Beilstein Handbook of Organic Chem., Reg. No. 660681, 1988.
International Search Report issued in PCT/US98/18189.
Dokunichin, Beilstein Handbook of Organic Chem., Reg. No. 530731, 1988.
Ullmann, Beilstein Handbook of Organic Chem. Reg. No. 222316, 1988.
Ullmann, Beilstein Handbook of Organic Chem. Reg. No. 254129, 1988.
Scholl, Beilstein Handbook of Organic Chem. Reg. No. 245245, 1988.
Bergmann, Beilstein Handbook of Organic, Chem. Reg. No. 13823,1988.
Abstr Pap Am Chem Soc 206 (2), 1993 Slama et al.
Abstract 1994:425593, 1994 Zailsev et al.
Aldrich Catalog #23,559–8, 1995.
Angew. Chem. 76:1,50, 1964 Baer et al.
Ann. 673:132–36, 1964 Reid et al.
Ann. Chem. 688:177–88, 1965 Reid et al.
Annu. Rev. Neurosci 13,171–82, 1990 Choi et al.
Anticancer Drug Design 10(6)507–14 (Sep.), 1995 Griffin et al.
Anti–Cancer Drug Design 10(6): 507–14, 1995 R. Griffin et al.
Anticancer Research 11:881–888, 1991 Sakagami et al.
Arch. Pharm. Ber. Dtsch. Pharm. Ges. 300:6, 533–39 1967 Reisch.
Beilstein Handbook of Organic Chem. Reg. No. 158523 1950.
Beilstein Handbook of Organic Chem. Reg. No. 233692 1956.
Beilstein Handbook of Organic Chem. Reg. No. 3140506 1998.
Beilstein Handbook of Organic Chem. Reg. No. 165349 1998.
Beilstein Handbook of Organic Chem. Reg. No. 161148 1998.
Beilstein Handbook of Organic Chem. Reg. No. 2213597 1999.
Biochemical and Biophysical Research Communications 136(3), 1110–15 1986 Tanuma et al.
Biochemical and Biophysical Research Communications 195, No. 2, 558–564 1993 Jesser et al.
Biochemical and Biophysical Research Communications 195(2), 558–64 1993 Jesser et al.
Biochemical and Biophysical Research Communications 210, No. 2, 329–337 1995 Aoki et al.
Biochemical and Biophysical Research Communications 220,411–17, 1996 Uchiumi et al.
Biochemical and Biophysical Research Communications 236, 265–69 1997 Maruta et al.
Biochemical Society Transactions vol. 8 (2), 192–193, 1980 Whitby et al.
Biochemistry 30, 5907–5912 1991 Maruta et al.
Biochemistry International 16, No. 3, 397–403 1988 Concha et al.
Biochemistry International 19, No. 6, 1395–1402 1989 Tanuma et al.
Biochemistry International 18, No. 4, 701–708 1989 Tanuma et al.
Biochemistry International 24, No. 5, 889–897 1991 Tsai et al.
Biochimica et Biophysica Acta 827, 228–234 1985 Tavassoli et al.
Biochimica et Biophysica Actas 1158, 251–56 1993 Aoki et al.
Bull. Chem. Soc. Jpn. 61(6):2238–40 1988. Sato et al.
Bull. Soc. Chim. Fr. 233, 1962 Granger et al.
C. R. Acad. Sci. 275:17,961–64, 1972 Michailidis et al.
Cell 94, 325–337, 1998 Kuida et al.
Cell 94, 399–352, 1998 Hakem et al.
Cell Biology and Toxicology 9, No. 2, 165–175, 1993 Clayson et al.
Chem Abstracts 52:17 (14606h) (Sep. 10), 1958 Orchiai et al.
Chem Abstracts 55:6 (5491ce) (Mar. 20), 1961 Ochiai et al.
Chem Abstracts 58:4 (3425d) (Feb. 18), 1963 Hayashi et al.
Chem Abstracts vol. 126, No.17,229493f (4/28/97), 1997 Angeliki.
Chem. Abstracts 64:695e, 1966 Ried et al.
Chem. Ber. 46, pp. 2087, 2089, 1913 Kardos.
Chemical Abstract 54:22648a, 1960 Nikitskaya et al.
Chemical Abstract vol. 51:1960, 1957 Taylor et al.
Chemical Abstract vol. 52:6285, 1958 Ohta.
Chemical Abstract vol. 52:4646, 1958 Gilman et al.
Chemical Abstract vol. 52:58846b, 1958 Gateff et al.
Chemical Abstract vol. 55:12868a, 1961.
Chemical Abstract vol. 55:112868b, 1961.
Chemical Abstract vol. 55:12686c, 1961.
Chemical Abstract vol. 59:10037 c, 1963 Hazard et al.
Chemical Abstract vol 61:15194, 1964 Tsuboi.
Chemical Abstract vol. 61:9494a, 1964 Dokunikhin et al.
Chemical Abstract vol. 61:9493f, 1964 Bodea et al.
Chemical Abstract vol. 61:13305g, 1964 Badger et al.
Chemical Abstract vol. 62:5259, 1965 Lakeside Lab., Inc.
Chemical Abstract vol. 63:4256, 1965 Keene et al.
Chemical Abstract vol. 62:9129g, 1965 Klosa.
Chemical Abstract vol. 65:15320a, 1966 Kametani.
Chemical Abstract vol. 65:15319h, 1966 Humber et al.
Chemical Abstract vol. 68:59420, 1968 Chandler et al.
Chemical Abstract vol. 70:3629 1969 Weis.
Chemical Abstract vol. 70:67988 1969 Resplandy et al.
Chemical Abstract vol. 70:4079 1969 Coyne et al.
Chemical Abstract vol. 73:35200 1970 Pan et al.
Chemical Abstract 72:121337 1970 Pan et al.
Chemical Abstract 74:110112y, (p. 252 May 10)1971 Damas.
Chemical Abstract vol. 78:123624 1973 Swenton et al.
Chemical Abstract vol. 78:68700 1973 Roehm et al.
Chemical Abstract vol. 78:58193 1973 Mondon et al.
Chemical Abstract vol. 78:84227, 1973 Kraatz et al.
Chemical Abstract vol. 78:29384, 1973 Forrester et al.
Chemical Abstract vol. 78:29593, 1973 Cerbai et al.
Chemical Abstract vol. 81:37489, 1974 Cerbai et al.
Chemical Abstract vol. 85:182, 1976 Tullar et al.
Chemical Abstract vol. 84:16943, 1976 Minatoya et al.
Chemical Abstract vol. 85:77216, 1976 Ege et al.
Chemical Abstract 85(1976), 159898a 1976.
Chemical Abstract vol. 87:5778, 1977 Fomenko et al.
Chemical Abstract vol. 82:30602, 1978 Minatoya et al.
Chemical Abstract vol. 90:6486t, 1979 Takahashi.
Chemical Abstract vol. 91:39035, 1979 Migachev.
Chemical Abstract vol. 92181104e, 1980 Ryabukhina et al.
Chemical Abstract vol. 92:41620, 1980 Migachev et al.
Chemical Abstract vol. 92:41511, 1980 Migachev et al.
Chemical Abstract 92:22393, 1980 Simmonds.
Chemical Abstract vol. 95:80661, 1981 Narasimhan et al.

Chemical Abstract vol. 95 (9):80666, 1981 Migachev et al.
Chemical Abstract vol. 95 (9):80666, 1981 Migachev et al.
Chemical Abstract vol. 95:80688, 1981 Migachev et al.
Chemical Abstract vol. 95:42867, 1981 Migachev et al.
Chemical Abstract vol. 95:42866, 1981 Migachev et al.
Chemical Abstract 187120, 1981 Migachev et al.
Chemical Abstract vol. 96:6539m, p. 592, 1982 Singh et al.
Chemical Abstract vol. 96:68519, 1982 Leardini et al.
Chemical Abstract vol. 97:126680, 1982 Grimshaw et al.
Chemical Abstract vol. 100:103453, 1984 Prostakov et al.
Chemical Abstract vol. 100:191713, 1984 Orlic–Nuber et al.
Chemical Abstract vol. 102:203854, 1985 Migachev et al.
Chemical Abstract vol. 105: 60505, 1986 Andrievskii et al.
Chemical Abstract vol. 106: (67553), 1987 Pellefier.
Chemical Abstract vol. 107:39655v, 1987 Bondarenko et al.
Chemical Abstract vol. 110:230971, 1989 Val'kova et al.
Chemical Abstract vol. 113:190649, 1990 Val'kova et al.
Chemical Abstract vol. 112:44716, 1990 Korol'kova et al.
Chemical Abstract vol. 112:128235, 1990 Korol'kova et al.
Chemical Abstract vol. 112:216749, 1990 Benson et al.
Chemical Abstract vol. 114:143456, 1991 Walser.
Chemical Abstract vol. 115: (232107), 1991 Nagao.
Chemical Abstract vol. 115:70731f, 1991 Donshikh et al.
Chemical Abstract vol. 115:158338, 1991 Buckman et al.
Chemical Abstract vol. 114:42543, 1991 Andrievskii et al.
Chemical Abstract vol. 119:72127, 1993 Zaitsev et al.
Chemical Abstract vol. 118:191567, 1993 Dow.
Chemical Abstract vol. 118:80722, 1993 Dininno et al.
Chemical Abstract vol. 118:101709, 1993 Dininno et al.
Chemical Abstract vol. 120:134231, 1994 Rocca et al.
Chemical Abstract vol. 121:220651v, 1994 Pawlowska et al.
Chemical Abstract vol. 121:172572, 1994 Liu et al.
Chemical Abstract vol. 120:95793, 1994 Kyota et al.
Chemical Abstract vol. 121:57315, 1994 Dow et al.
Chemical Abstract vol. 120:148508p, 1994 Barros et al.
Chemical Abstract vol. 123:505, 1995 Weltin et al.
Chemical Abstract vol. 122:10865, 1995 Lamba et al.
Chemical Abstract vol. 122:170499, 1995 Korol'kova et al.
Chemical Abstract vol. 123:256711, 1995 Kalindjan et al.
Chemical Abstract vol. 122:170250, 1995 Gorio et al.
Chemical Abstract vol. 122:187249, 1995 Dininno et al.
Chemical Abstract 122:316902, 1995 Desilets et al.
Chemical Abstract 122:316901, 1995 Desilets et al.
Chemical Abstract 122:187526, 1995 Langlois et al.
Chemical Abstract vol. 125:87882, 1996 Yamaguchi et al.
Chemical Abstract vol. 124:331706, 1996 Silverman et al.
Chemical Abstract vol. 126:115554, 1996 Malhotra et al.
Chemical Abstract vol. 125:246943, 1996 Korol'kova et al.
Chemical Abstract vol. 125:277462, 1996 Ge et al.
Chemical Abstract 124:202047, 1996 Fernandez et al.
Chemical Abstract vol. 128:36109, 1997 Sakai et al.
Chemical Abstract vol. 127:234258, 1997 Reddy et al.
Chemical Abstract vol. 127:81282, 1997 Marek et al.
Chemical Abstract vol. 128:34752, 1997 Jones et al.
Chemical Abstract vol. 127:80243, 1997 Banister et al.
Chemical Abstract abstract no. 17462, 1998 Yoshida et al.
Chemical Abstract vol. 129:104224, 1998 West.
Chemical Abstract vol. 128:138099, 1998 Weltin et al.
Chemical Abstract vol. 130:24816, 1998 Park et al.
Chemical Abstract vol. 128:75320, 1998 Jones et al.
Chemical Abstract vol. 128:165850, 1998 Cookson et al.
Chemical Abstract vol. 129:54301, 1998 Albright et al.
Chemical Abstract No. 816103, 1998 Albright et al.
Chemical Abstracts vol. 52 (21) 18420d, 1958 Tanida.

Chemical Abstracts vol. 62, no. 5, 5271c, Mar. 1965.
Chemical Abstracts vol. 76 (25) 153704b, 1972 Pozharskii et al.
Chemical Abstracts vol. 88 (7) 49887, 1978 Szadowski.
Chemical Abstracts 88, No. 13, 505 (88:89502c), 1978 Dokunikhin et al.
Chemical Abstracts 94, No. 23, 637(192098y), 1981 Migachev.
Chemical Abstracts Registry No. 17 1399–15–8, 1998.
Chemical Abstracts Registry No. 14223 8–47–9, 1998.
Chemical Abstracts 85:159898a 85, No. 21, 531, 1974 Upadysheva et al.
Chemical and Pharmaceutical Bulletin vol. 26, No. 12, pp. 3682–94, 1978 Hamada et al.
Chemische Berichte vol. 102, 1161–1176, 1969 Kauffmann et al.
Gazz. Chim. Ital. 91:1345–51, 1962 Di Maio et al.
Gazz. Chim. Ital. 91:1124–32, 1962 Di Maio et al.
Gazz. Chim. Ital. 94:5, 590–94, 1964 Di Maio et al.
Hawleys Chemical Condense Dictionary Sax (Ed) 11th Ed, 1987 p. 898, 1987 Hawley's.
Heterocycles 22:2,237–40, 1984 Naito et al.
Int. J. Immunopharmac 17, No. 4, 265–271, 1995 Weltin et al.
IS&T's Tenth Int'l Congress on Advances in Non–Impact Printing Technologies 246–248, 1994 Richter et al.
ISR for PCT/US98/18185, 1998.
ISR for PCT/US98/18186, 1998.
ISR for PCT/US98/18187, 1998.
ISR for PCT/US98/18188, 1998.
ISR for PCT/US98/18189, 1998.
ISR for PCT/US98/18195, 1998.
ISR for PCT/US98/18196, 1998.
ISR for PCT/US98/18226, 1998.
ISR for PCT/US98/30971, 1998.
ISR for PCT/US99/30971 1998.
Itsu Kenkusho Nempo 16:15–23, 1971 Ochiai et al.
J Chem. Soc. 11:1293–97, 1978 Davies et al.
J. Am. Chem. Soc. 78:5104–8, 1956 Taylor et al.
J. Biol. Chem. 246(20), 6362–64, 1972 Miwa et al.
J. Biol. Chem. 261 (32), 14902–11, 1986 Hatakeyama et al.
J. Biol. Chem. 262(36), 17641–50, 1987 Ikejima et al.
J. Biol. Chem. 262(23), 11037–40, 1988 Ikejima et al.
J. Biol. Chem. 267(20), 14436–42, 1992 Tsai et al.
J. Chem. Soc. 12:2231–2241, 1971 Barton.
J. Chem. Res., Synop. 8:302, 1995 Mueller et al.
J. Chem. Res., Synop. 21–26, 1996 Mueller et al.
J. Chem. Soc. pp.1979–1984, 1929 Blount et al.
J. Chem. Soc. 1624–28, 1958 Johnson.
J. Chem. Soc. 4295–98, 1962 Brown et al.
J. Chem. Soc. 1:14, 1747–51, 1974 Ninomiya et al.
J. Chem Soc. 1:7, 763–70, 1974 Bailey et al.
J. Exp. Med. vol. 186, No. 7, Oct. 6, 1997, 1041–9, 1997 Szabo.
J. Het. Chem. vol. 7, pp. 597–605, 1970 Pan et al.
J. Heterocycl. Chem. 20:5, 1407–9, 1983 Rougeot et al.
J. Med. Chem. 38, 389–393, 1995 Slama et al.
J. Med. Chem. 38, 4332–4336, 1995 Slama et al.
J. Neuroscience Res. 47: 372–383, 1997 Ceruti et al.
J. Biological Chemistry 261 (2), 965–69, 1986 Tanuma et al.
J. Org. Chem. 29:3, 681–85, 1964 Masamune et al.
J. Org. Chem. 47, 2043–2047, 1982 Taylor et al.
J. Org. Chem. vol. 23, pp. 1071–2 Jul., 1958 Robinson et al.
J. Org. Chem. 29:11, 3180–85, 1964 Baer et al.

J. Org. Chem. 43, 11, 2190–96, 1978 Eisch et al.
JACS 71:937–8 (Mar), 1949 Wilson et al.
JACS 76:4396–8 (Sep 5), 1954 Wright.
JCS pp. 4067–75, 1952 Peak et al.
JCS pp. 1294–304, 1956 Albert et al.
JCS pp. 2384–96, 1959 Albert et al.
Journal of Cellular Biochemistry 29:361–372, 1985 Bolander, Jr.
Journal of Cerebral Blood Flow and Metabolism 17 No. 11, 1137–1142, 1997 Takahashi et al.
Journal of Heterocyclic Chemistry vol. 3, pp. 466–9 Dec., 1966 Aparajithan.
Journal of Heterocyclic Chemistry vol. 15, pp. 1513–4, 1978 Nuvole et al.
Journal of Medicinal Chemistry vol. 20 (3) 449–452, 1977 Diana et al.
Journal of Neurochemistry 70, No. 2, 501–508, 1988 Cookson et al.
Journal of Organic Chemistry vol. 11, No. 3, 239–246, 1946 Bergstrom et al.
Journal of Organic Chemistry 53(20);4650–3, 1988 D. Dumas.
Journal of Chemical Society pp. 1799–1803 1972, Singh et al.
Journal of the Chemical Society vol. 9, 944–950, 1976 Loewenthal et al.
Justus Liebigs Ann. Chem. 388, p.212, 1912 Ullmann et al.
Med. Chem. Res. 6:2, 81–101, 1996 Castan et al.
Mutation Research 218,67–74, 1989 Gonzalez et al.
Mutation Research 350, 25–34, 1996 Wachsman.
Nature Medicine JHU, 1997 Eliasson et al.
Neuron 1, 623–634, 1988 Choi.
Pharm. Bull. 5:289–91, 1957 Ochiai et al.
Phosphorus Sulfur vol. 14, No. 1, pp. 131–8, 1983 Becher et al.
Ric. Sci. 38:3, 231–33, 1988 Di Maio et al.
Rocz. Chem. 41:1,89–101, 1967 Schoen et al.
Science 282, 1484–1487, 1998 Smith et al.
Spin Label Analogue of ATP 246, No. 20, 6362–6364, 1971 Miwa et al.
Switzerland Patent 601 246, 1978.
Tetrahedron supp. 8, part 1, pp. 305–12, 1966 Tamayo et al.
Tetrahedron Letters 32,No. 35, 4525–4528, 1991 Chida et al.
Tetrahedron Letters 36:33, 5983–86, 1995 White et al.
Tetrahedron Letters 52:9, 3117–34, 1996 White et al.
The Journal of Biological Chemistry 242, No. 22, 5301–5307, 1967 Futai et al.
The Journal of Biological Chemistry vol. 257, No. 21, 12872–12877, 1982 Wielckens et al.
The Journal of Biological Chemistry 259, No. 2, 986–995, 1984 Oka et al.
The Journal of Biological Chemistry 261, No.2, pp. 965–969, 1986 Tanuma et al.
The Journal of Biological Chemistry 263, No. 23, 11037–11040, 1988 Ikejima et al.
The Journal of Biological Chemistry 272, No. 18, 11895–11901, 1997 Lin et al.
TiPS 11, 379–387, 1990 Meldrum et al.
TIPS in press, 1998 Pieper et al.
Vertex Pharmaceuticals Inc. PR Newswire, 1998.

COMPOUNDS, METHODS AND PHARMACEUTICAL COMPOSITIONS FOR TREATING NEURAL OR CARDIOVASCULAR TISSUE DAMAGE

This application is a continuation-in-part application of U.S. Ser. No. 08/922,548, filed Sep. 3, 1997, entitled "Poly (ADP-Ribose)Polymerase Inhibitors for Treating Neural or Cardiovascular Tissue Damage Using the Same".

BACKGROUND OF THE INVENTION

1. Field of the Invention

The invention relates to the prevention and treatment of neural or cardiovascular tissue damage resulting from ischemia and reperfusion injury. More particularly, the invention concerns the prevention or treatment of vascular stroke by administering inhibitors of the nucleic enzyme poly(ADP-ribose) polymerase or "PARP", which is also sometimes called "PARS" for poly(ADP-ribose) synthetase.

2. Description of the Prior Art

Poly(ADP-ribose) polymerase ("PARP") is an enzyme located in the nuclei of cells of various organs, including muscle, heart and brain cells. PARP plays a physiological role in the repair of strand breaks in DNA. Once activated by damaged DNA fragments, PARP catalyzes the attachment of up to 100 ADP-ribose units to a variety of nuclear proteins, including histones and PARP itself. While the exact range of functions of PARP has not been established, this enzyme is thought to play a role in enhancing DNA repair.

During major cellular stresses, however, the extensive activation of PARP can rapidly lead to cell death through depletion of energy stores. Four molecules of ATP are consumed for every molecule of NAD (the source of ADP-ribose) regenerated. Thus, NAD, the substrate of PARP, is depleted by massive PARP activation and, in the efforts to re-synthesize NAD, ATP may also be depleted.

PARP activation plays a key role in both NMDA- and NO-induced neurotoxicity, as shown by the use of PARP inhibitors to prevent such toxicity in cortical cultures in proportion to their potencies as inhibitors of this enzyme (Zhang et al., "Nitric Oxide Activation of Poly(ADP-Ribose) Synthetase in Neurotoxicity", Science, 263:687–89 (1994)) and in hippocampal slices (Wallis et al., "Neuroprotection Against Nitric Oxide Injury with Inhibitors of ADP-Ribosylation", NeuroReport, 5:3, 245–48 (1993)). The potential role of PARP inhibitors in treating neurodegenerative diseases has thus been known.

Large numbers of known PARP inhibitors have been described in Banasik et al., "Specific Inhibitors of Poly (ADP-Ribose) Synthetase and Mono(ADP-Ribosyl) transferase", J. of Biol. Chem., 267:3, 1569–75 (1992), and in Banasik et al., "Inhibitors and Activators of ADP-Ribosylation Reactions", Molec. and Cell. Biochem. 138:185–97 (1994).

It has been demonstrated that single injections of PARP inhibitors have reduced the infarct size caused by ischemia and reperfusion of the heart or skeletal muscle in rabbits. In these studies, a single injection of the PARP inhibitor, 3-aminobenzamide (10 mg/kg), either one minute before occlusion or one minute before reperfusion, caused similar reductions in infarct size in the heart (32–42%). Another PARP inhibitor, 1,5-dihydroxyisoquinoline (1 mg/kg), reduced infarct size by a comparable degree (38–48%). Thiemermann et al., "Inhibition of the Activity of Poly(ADP Ribose) Synthetase Reduces Ischemia-Reperfusion Injury in the Heart and Skeletal Muscle", Proc. Natl. Acad. Sci. USA, 94:679–83 (1997). This finding has suggested that PARP inhibitors might be able to salvage previously ischemic heart or skeletal muscle tissue.

PARP activation has also been shown to provide an index of damage following neurotoxic insults by glutamate (via NMDA receptor stimulation), reactive oxygen intermediates, amyloid β-protein, n-methyl-4-phenyl-1,2,3, 6-tetrahydropyridine (MPTP) and its active metabolite N-methyl-4-phenylpyridine (MPP$^+$), which participate in such pathological conditions as stroke, Alzheimer's disease and Parkinson's disease. Zhang et al., "Poly(ADP-Ribose) Synthetase Activation: An Early Indicator of Neurotoxic DNA Damage", J. of Neurochem., 65:3, 1411–14 (1995).

Neural damage following stroke and other neurodegenerative processes is thought to result from a massive release of the excitatory neurotransmitter glutamate, which acts upon the N-methyl-D-aspartate (NMDA) receptors and other subtype receptors. Evidence includes findings in many animal species, as well as in cerebral cortical cultures treated with glutamate or NMDA, that glutamate receptor antagonists block neural damage following vascular stroke. Dawson et al., "Protection of the Brain from Ischemia", Cerebrovascular Disease, 319–25 (Batjer ed. 1997).

The stimulation of NMDA receptors, in turn, activates the enzyme neuronal nitric oxide synthase (nNOS), which causes the formation of nitric oxide (NO), which more directly mediates neurotoxicity. Protection against NMDA neurotoxicity has occurred following treatment with NOS inhibitors. See Dawson et al., "Nitric Oxide Mediates Glutamate Neurotoxicity in Primary Cortical Cultures", Proc. Natl. Acad. Sci. USA, 88:6368–71 (1991); and Dawson et al., "Mechanisms of Nitric Oxide-mediated Neurotoxicity in Primary Brain Cultures", J. Neurosci., 13:6, 2651–61 (1993). Protection against NMDA neurotoxicity can also occur in cortical cultures from mice with targeted disruption of nNOS. See Dawson et al., "Resistance to Neurotoxicity in Cortical Cultures from Neuronal Nitric Oxide Synthase-Deficient Mice", J. Neurosci., 16:2479–87 (1996). It is known that neural damage following vascular stroke is markedly diminished in animals treated with NOS inhibitors or in mice with nNOS gene disruption. Iaddcola, "Bright and Dark Sides of Nitric Oxide in Ischemic Brain Injury", Trends Neurosci. 20:3, 132–39 (1997); and Huang et al., "Effects of Cerebral Ischemia in Mice Deficient in Neuronal Nitric Oxide Synthase", Science, 265:1883–85 (1994). See Beckman et al., "Pathological Implications of Nitric Oxide, Superoxide and Peroxynitrite Formation", Biochem. Soc. Trans., 21:330–34 (1993). Either NO or peroxynitrite can cause DNA damage, which activates PARP.

Zhang et al., U.S. Pat. No. 5,587,384 issued Dec. 24, 1996 discusses the use of certain PARP inhibitors, such as benzamide and 1,5-dihydroxyisoquinoline, to prevent NMDA-mediated neurotoxicity and, thus, treat stroke, Alzheimer's disease, Parkinson's disease and Huntington's disease. See also, Zhang et al. "Nitric Oxide Activation of Poly(ADP-Ribose) Synthetase in Neurotoxicity", Science, 263:687–89 (1994).

However, the approach of using these PARP inhibitors to reduce NMDA-receptor stimulation or to treat or prevent tissue damage caused by NO is limited in effect. For example, side effects have been observed with some of the best-known PARP inhibitors, as discussed in Milam et al., "Inhibitors of Poly(Adenosine Diphosphate-Ribose) Synthesis: Effect on Other Metabolic Processes", Science, 223:589–91 (1984). Specifically, the PARP inhibitors 3-aminobenzamide and benzamide not only inhibited the action of PARP but also were shown to affect cell viability, glucose metabolism, and DNA synthesis. Thus, it was concluded that the usefulness of these PARP inhibitors may be severely restricted by the difficulty of finding a dose small enough to inhibit the enzyme without producing additional metabolic effects.

Certain related compounds have been disclosed for medical treatments and other uses. However, these compounds are structurally distinguishable and directed to uses which emphasize their toxic characteristics. Fernandez et al., PCT publication WO 95/29895, discloses an isoquinoline derivative which is used as an anticancer agent. Desilets et al., "Design and Synthesis of Near-Infrared Absorbing Pigments", *Can. J. Chem.* (1995), 73:3, 319–35, disclose the design and synthesis of near-infrared absorbing pigments such as aceanthrene green and derivatives. Langlois et al., "Synthesis of Quinazoline-2,4-dione and Naphthalimide Derivatives as New S-HT$_3$ Receptor Antagonists", *Eur. J. Med. Chem.* (1994), 29:12, 925–940, disclose the preparation and 5-HT$_3$ receptor antagonist activity of certain quinazolinediones, benzisoquinolinones, and -diones. Simmonds, British Patent GB1545767 (1975) disclose benzopyranoisoquinoline derivatives useful for antiinflammatory and central nervous system activity and also disclose a related compound useful only as an intermediate in making these distinct compounds. Kardos et al., German Patent D.R.P. 282711, disclose structurally distinct but related chlorinated compounds.

Accordingly, there remains a need for a composition containing PARP inhibitors that produce more potent and reliable effects, particularly with respect to neural or cardiovascular tissue damage and vascular stroke, and less side effects.

SUMMARY OF THE INVENTION

The present invention relates to novel poly(ADP-ribose) polymerase ("PARP") inhibitors and methods for effecting a neuronal activity in an animal using the same. The invention also relates to methods of treating and/or preventing neural or cardiovascular tissue damage resulting from cerebral ischemia and reperfusion injury by administering the compounds of the present invention. The invention further relates to methods of treating vascular stroke by administering the compounds of the present invention.

The invention also relates to methods of treating neurodegenerative diseases and to methods of treating cardiovascular diseases in an animal by administering to said animal an effective amount of the compounds of the present invention. The invention also contemplates the use of an embodied compound for treating a neurological disorder or a cardiovascular disease in an animal.

The invention also contemplates the use of an embodied compound in the preparation of a medicament for the treatment of a neurological disease or a cardiovascular disease in an animal.

Preferred inhibitors of poly(ADP-ribose) polymerase have an IC$_{50}$ for inhibiting poly(ADP-ribose) polymerase in vitro of 100 μM or lower. Specifically, the present invention relates to a compound of formula I:

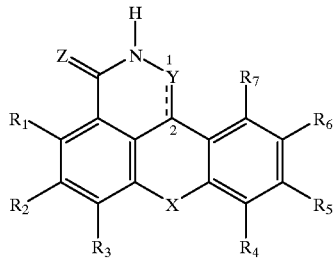

or a pharmaceutically acceptable salt, hydrate, prodrug, or a mixture thereof, wherein
 Y is alkylhalo, alkyl-CO-G, COG, a direct bond, C=O, O, NR$_8$, or CR$_8$;
 G is NR$_9$R$_{10}$, OR$_9$, SR$_9$, or R$_9$;
 Z is O, S, or NR$_{11}$;
 X is NR$_{12}$, O, S, CR$_{12}$R$_{13}$, or C=O;
 R$_1$, R$_2$, R$_3$, R$_4$, R$_5$, R$_6$, R$_7$, R$_8$, R$_9$, R$_{10}$, R$_{11}$, R$_{12}$, or R$_{13}$ are independently:
  hydrogen, halo, alkylhalo, hydroxy, C$_1$–C$_9$ straight or branched chain alkyl, C$_2$–C$_9$ straight or branched chain alkenyl group, C$_3$–C$_8$ cycloalkyl, C$_5$–C$_7$ cycloalkenyl, Ar$_1$, amino, nitro, nitroso, or carboxy,
 wherein said alkyl, alkenyl, cycloalkyl, cycloalkenyl, and Ar$_1$ groups are independently unsubstituted or substituted with one or more substituent(s) independently selected from the group consisting of C$_3$–C$_8$ cycloalkyl, C$_5$–C$_7$ cycloalkenyl, halo, hydroxyl, nitro, trifluoromethyl, C$_1$–C$_6$ straight or branched chain alkyl, C$_2$–C$_6$ straight or branched chain alkenyl, C$_1$–C$_4$ alkoxy, C$_2$–C$_4$ alkenyloxy, phenoxy, benzyloxy, and Ar$_2$, and wherein Ar$_1$ and Ar$_2$ are independently 1-naphthyl, 2-naphthyl, 2-indolyl, 3-indolyl, 4-indolyl, 2-furyl, 3-furyl, tetrahydrofuranyl 2-thienyl, 3-thienyl, 4-thienyl, 2-pyridyl, 3-pyridyl, 4-pyridyl, or phenyl, each having one or more substituent(s) independently selected from the group consisting of hydrogen, halo, hydroxyl, nitro, trifluoromethyl, C$_1$–C$_6$ straight or branched chain alkyl, C$_2$–C$_6$ straight or branched chain alkenyl, C$_1$–C$_4$ alkoxy or C$_2$–C$_4$ alkenyloxy, phenoxy, and benzyloxy; and with the proviso that when Y is CH or CCH$_3$ and there is a double bond between C$_1$ and C$_2$, and R$_1$–R$_7$ are H, then X is not O.

A preferred embodiment of this invention is a compound of formula II:

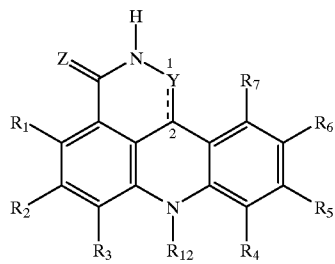

or a pharmaceutically acceptable salt, hydrate, prodrug, or a mixture thereof, wherein
 Y is alkylhalo, alkyl-CO-G, COG, a direct bond, C=O, O, NR$_8$, or CR$_8$;
 G is NR$_9$R$_{10}$, OR$_9$, SR$_9$, or R$_9$;
 Z is O, S, or NR$_{11}$; and $R_1$, $R_2$, $R_3$, $R_4$, $R_5$, $R_6$, $R_7$, $R_8$, $R_9$, $R_{10}$, or $R_{11}$ are independently:

hydrogen, halo, alkylhalo, hydroxy, $C_1$–$C_9$ straight or branched chain alkyl, $C_2$–$C_9$ straight or branched chain alkenyl group, $C_3$–$C_8$ cycloalkyl, $C_1$–$C_7$ cycloalkenyl, $Ar_1$, amino, nitro, nitroso, or carboxy, wherein said alkyl, alkenyl, cycloalkyl, cycloalkenyl, and $Ar_1$ groups are independently unsubstituted or substituted with one or more substituent(s) independently selected from the group consisting of $C_3$–$C_8$ cycloalkyl, $C_5$–$C_7$ cycloalkenyl, halo, hydroxyl, nitro, trifluoromethyl, $C_1$–$C_6$ straight or branched chain alkyl, $C_2$–$C_6$ straight or branched chain alkenyl, $C_1$–$C_4$ alkoxy, $C_2$–$C_4$ alkenyloxy, phenoxy, benzyloxy, and $Ar_2$, and wherein $Ar_1$ and $Ar_2$ are independently 1-naphthyl, 2-naphthyl, 2-indolyl, 3-indolyl, 4-indolyl, 2-furyl, 3-furyl, tetrahydrofuranyl 2-thienyl, 3-thienyl, 4-thienyl, 2-pyridyl, 3-pyridyl, 4-pyridyl, or phenyl, each having one or more substituent(s) independently selected from the group consisting of hydrogen, halo, hydroxyl, nitro, trifluoromethyl, $C_1$–$C_6$ straight or branched chain alkyl, $C_2$–$C_6$ straight or branched chain alkenyl, $C_1$–$C_4$ alkoxy or $C_2$–$C_4$ alkenyloxy, phenoxy, and benzyloxy.

Another preferred embodiment of this invention is a compound of formula III:

III or a pharmaceutically acceptable salt, hydrate, prodrug, or a mixture thereof, wherein Y is alkylhalo, alkyl-CO-G, COG, a direct bond, C=O, O, $NR_8$, or $CR_8$;

G is $NR_9R_{10}$, $OR_9$, $SR_9$, or $R_9$;

Z is O, S, or $NR_{11}$; and $R_1$, $R_2$, $R_3$, $R_4$, $R_5$, $R_6$, $R_7$, $R_8$, $R_9$, $R_{10}$, or $R_{11}$ are independently:

hydrogen, halo, alkylhalo, hydroxy, $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, $Ar_1$, amino, nitro, nitroso, or carboxy, wherein said alkyl, alkenyl, cycloalkyl, cycloalkenyl, and $Ar_1$ groups are independently unsubstituted or substituted with one or more substituent(s) independently selected from the group consisting of $C_3$–$C_8$ cycloalkyl, $C_5$–$C_7$ cycloalkenyl, halo, hydroxyl, nitro, trifluoromethyl, $C_1$–$C_6$ straight or branched chain alkyl, $C_2$–$C_6$ straight or branched chain alkenyl, $C_1$–$C_4$ alkoxy, $C_2$–$C_4$ alkenyloxy, phenoxy, benzyloxy, and $Ar_2$, and wherein $Ar_1$ and $Ar_2$ are independently 1-naphthyl, 2-naphthyl, 2-indolyl, 3-indolyl, 4-indolyl, 2-furyl, 3-furyl, tetrahydrofuranyl 2-thienyl, 3-thienyl, 4-thienyl, 2-pyridyl, 3-pyridyl, 4-pyridyl, or phenyl, each having one or more substituent(s) independently selected from the group consisting of hydrogen, halo, hydroxyl, nitro, trifluoromethyl, $C_1$–$C_6$ straight or branched chain alkyl, $C_2$–$C_6$ straight or branched chain alkenyl, $C_1$–$C_4$ alkoxy or $C_2$–$C_4$ alkenyloxy, phenoxy, and benzyloxy.

A further preferred embodiment of this invention is a compound of formula IV:

IV or a pharmaceutically acceptable salt, hydrate, prodrug, or a mixture thereof, wherein Y is alkylhalo, alkyl-CO-G, COG, a direct bond, C=O, O, $NR_8$, or $CR_8$;

G is $NR_9R_{10}$, $OR_9$, $SR_9$, or $R_9$;

Z is O, S, or $NR_{11}$; and $R_1$, $R_2$, $R_3$, $R_4$, $R_5$, $R_6$, $R_7$, $R_8$, $R_9$, $R_{10}$, $R_{11}$, $R_{12}$, or $R_{13}$ are independently:

hydrogen, halo, alkylhalo, hydroxy, $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, $Ar_1$, amino, nitro, nitroso, or carboxy, wherein said alkyl, alkenyl, cycloalkyl, cycloalkenyl, and $Ar_1$ groups are independently unsubstituted or substituted with one or more substituent(s) independently selected from the group consisting of $C_3$–$C_8$ cycloalkyl, $C_5$–$C_7$ cycloalkenyl, halo, hydroxyl, nitro, trifluoromethyl, $C_1$–$C_6$ straight or branched chain alkyl, $C_2$–$C_6$ straight or branched chain alkenyl, $C_1$–$C_4$ alkoxy, $C_2$–$C_4$ alkenyloxy, phenoxy, benzyloxy, and $Ar_2$, and wherein $Ar_1$ and $Ar_2$ are independently 1-naphthyl, 2-naphthyl, 2-indolyl, 3-indolyl, 4-indolyl, 2-furyl, 3-furyl, tetrahydrofuranyl 2-thienyl, 3-thienyl, 4-thienyl, 2-pyridyl, 3-pyridyl, 4-pyridyl, or phenyl, each having one or more substituent(s) independently selected from the group consisting of hydrogen, halo, hydroxyl, nitro, trifluoromethyl, $C_1$–$C_6$ straight or branched chain alkyl, $C_2$–$C_6$ straight or branched chain alkenyl, $C_1$–$C_4$ alkoxy or $C_2$–$C_4$ alkenyloxy, phenoxy, and benzyloxy.

A further preferred embodiment of this invention is a compound of formula V:

V or a pharmaceutically acceptable salt, hydrate, prodrug, or a mixture thereof, wherein Y is alkylhalo, alkyl-CO-G, COG, a direct bond, C=O, O, $NR_8$, or $CR_8$;

G is $NR_9R_{10}$, $OR_9$, $SR_9$, or $R_9$;

Z is O, S, or $NR_{11}$; and $R_1$, $R_2$, $R_3$, $R_4$, $R_5$, $R_6$, $R_7$, $R_8$, $R_9$, $R_{10}$, or $R_{11}$ are independently:

hydrogen, halo, alkylhalo, hydroxy, $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, $Ar_1$, amino, nitro, nitroso, or carboxy, wherein said alkyl, alkenyl, cycloalkyl, cycloalkenyl, and $Ar_1$ groups are independently unsubstituted or substituted with one or more substituent(s) independently selected from the group consisting of $C_3$–$C_8$ cycloalkyl, $C_5$–$C_7$ cycloalkenyl, halo, hydroxyl, nitro, trifluoromethyl, $C_1$–$C_6$ straight or branched chain alkyl, $C_2$–$C_6$ straight or branched chain alkenyl, $C_1$–$C_4$ alkoxy, $C_2$–$C_4$ alkenyloxy, phenoxy, benzyloxy, and $Ar_2$, and wherein $Ar_1$ and $Ar_2$ are independently 1-naphthyl, 2-naphthyl, 2-indolyl, 3-indolyl, 4-indolyl, 2-furyl, 3-furyl, tetrahydrofuranyl 2-thienyl, 3-thienyl, 4-thienyl, 2-pyridyl, 3-pyridyl, 4-pyridyl, or phenyl, each having one or more substituent(s) independently selected from the group consisting of hydrogen, halo, hydroxyl, nitro, trifluoromethyl, $C_1$–$C_6$ straight or branched chain alkyl, $C_2$–$C_6$ straight or branched chain alkenyl, $C_1$–$C_4$ alkoxy or $C_2$–$C_4$ alkenyloxy, phenoxy, and benzyloxy.

A further preferred embodiment of this invention is a compound of formula VI:

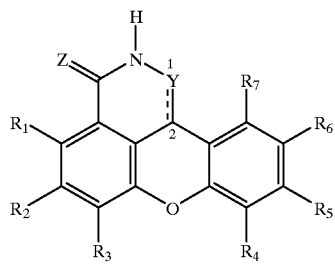

VI or a pharmaceutically acceptable salt, hydrate, prodrug, or a mixture thereof, wherein Y is alkylhalo, alkyl-CO-G, COG, a direct bond, C=O, O, $NR_8$, or $CR_8$;

G is $NR_9R_{10}$, $OR_9$, $SR_9$, or $R_9$;

Z is O, S, or $NR_{11}$;

$R_1$, $R_2$, $R_3$, $R_4$, $R_5$, $R_6$, $R_7$, $R_8$, $R_9$, $R_{10}$, or $R_{11}$ are independently:

hydrogen, halo, alkylhalo, hydroxy, $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, $Ar_1$, amino, nitro, nitroso, or carboxy, wherein said alkyl, alkenyl, cycloalkyl, cycloalkenyl, and $Ar_1$ groups are independently unsubstituted or substituted with one or more substituent(s) independently selected from the group consisting of $C_3$–$C_8$ cycloalkyl, $C_5$–$C_7$ cycloalkenyl, halo, hydroxyl, nitro, trifluoromethyl, $C_1$–$C_6$ straight or branched chain alkyl, $C_2$–$C_6$ straight or branched chain alkenyl, $C_1$–$C_4$ alkoxy, $C_2$–$C_4$ alkenyloxy, phenoxy, benzyloxy, and $Ar_2$, and wherein $Ar_1$ and $Ar_2$ are independently 1-naphthyl, 2-naphthyl, 2-indolyl, 3-indolyl, 4-indolyl, 2-furyl, 3-furyl, tetrahydrofuranyl, 2-thienyl, 3-thienyl, 4-thienyl, 2-pyridyl, 3-pyridyl, 4-pyridyl, or phenyl, each having one or more substituent(s) independently selected from the group consisting of hydrogen, halo, hydroxyl, nitro, trifluoromethyl, $C_1$–$C_6$ straight or branched chain alkyl, $C_2$–$C_6$ straight or branched chain alkenyl, $C_1$–$C_4$ alkoxy or $C_2$–$C_4$ alkenyloxy, phenoxy, and benzyloxy; and with the proviso that when Y is CH or $CCH_3$ and there is a double bond between $C_1$ and $C_2$, $R_1$–$R_7$ cannot all be H.

A further preferred embodiment of this invention is a compound of formula VII:

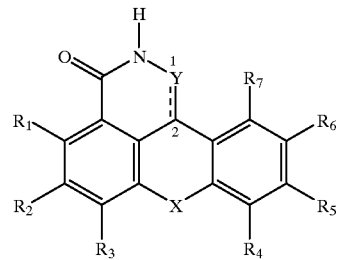

VII or a pharmaceutically acceptable salt, hydrate, prodrug, or a mixture thereof, wherein Y is O, $NR_8$, C=O or a direct bond;

X is $NR_{12}$, O, or S; and $R_1$, $R_2$, $R_3$, $R_4$, $R_5$, $R_6$, $R_7$, $R_8$, or $R_{12}$ are independently hydrogen, $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, or $Ar_1$, wherein said alkyl, alkenyl, cycloalkyl, cycloalkenyl and $Ar_1$ groups are independently unsubstituted or substituted with one or more substituent(s) independently selected from the group consisting of $C_3$–$C_8$ cycloalkyl, $C_1$–$C_7$ cycloalkenyl, halo, hydroxyl, nitro, trifluoromethyl, $C_1$–$C_6$ straight or branched chain alkyl, $C_2$–$C_6$ straight or branched chain alkenyl, $C_1$–$C_4$ alkoxy, $C_2$–$C_4$ alkenyloxy, phenoxy, benzyloxy, and $Ar_2$, and wherein $Ar_1$ and $Ar_2$ are independently 1-naphthyl, 2-naphthyl, 2-indolyl, 3-indolyl, 4-indolyl, 2-furyl, 3-furyl, tetrahydrofuranyl, 2-thienyl, 3-thienyl, 4-thienyl, 2-pyridyl, 3-pyridyl, 4-pyridyl, or phenyl, each having one or more substituent(s) independently selected from the group consisting of hydrogen, halo, hydroxyl, nitro, trifluoromethyl, $C_1$–$C_6$ straight or branched chain alkyl, $C_2$–$C_6$ straight or branched chain alkenyl, $C_1$–$C_4$ alkoxy or $C_1$–$C_4$ alkenyloxy, phenoxy, and benzyloxy.

The following are particularly preferred compounds of the present invention:

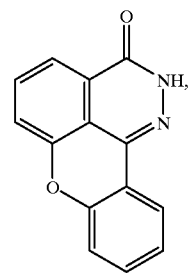

VIII

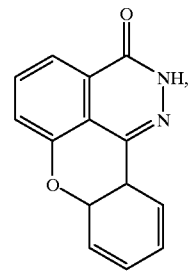

IX

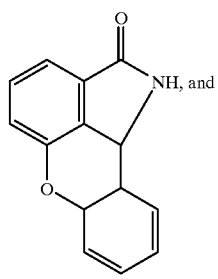

X

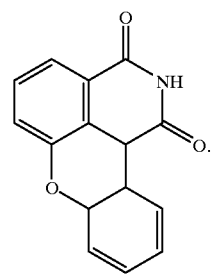

XI

DETAILED DESCRIPTION OF THE INVENTION

The present invention pertains to methods of using poly (ADP-ribose) polymerase (PARP) inhibitors for the treatment of a neurological disorder or a cardiovascular disease in an animal.

What the inventors have now discovered is that selected PARP inhibitors can ameliorate neural tissue damage and cardiovascular tissue damage, including that following focal ischemia, myocardial infarction, and reperfusion injury. Generally, inhibition of PARP activity spares the cell from energy loss, preventing irreversible depolarization of the neurons and, thus, provides neuroprotection. While not wishing to be bound thereby, it is thought that PARP activation may play a common role in still other excitotoxic mechanisms, perhaps as yet undiscovered, in addition to the production of free radicals and NO.

Definitions

"Alkyl" means a branched or unbranched saturated hydrocarbon chain comprising a designated number of carbon atoms. For example, $C_1$–$C_6$ straight or branched alkyl hydrocarbon chain contains 1 to 6 carbon atoms, and includes but is not limited to substituents such as methyl, ethyl, propyl, iso-propyl, butyl, iso-butyl, tert-butyl, n-pentyl, n-hexyl, and the like, unless otherwise indicated.

"Alkenyl" means a branched or unbranched unsaturated hydrocarbon chain comprising a designated number of carbon atoms. For example, $C_2$–$C_6$ straight or branched alkenyl hydrocarbon chain contains 2 to 6 carbon atoms having at least one double bond, and includes but is not limited to substituents such as ethenyl, propenyl, isopropenyl, butenyl, iso-butenyl, tert-butenyl, n-pentenyl, n-hexenyl, and the like, unless otherwise indicated.

"Alkoxy", means the group —OR wherein R is alkyl as herein defined. Preferably, R is a branched or unbranched saturated hydrocarbon chain containing 1 to 6 carbon atoms.

"Cyclo", used herein as a prefix, refers to a structure characterized by a closed ring.

"Halo" means at least one fluoro, chloro, bromo, or iodo moiety, unless otherwise indicated.

"Amino" compounds include amine ($NH_2$) as well as substituted amino groups comprising alkyls of one through six carbons.

"Ar", means an aryl or heteroaryl moiety which is substituted or unsubstituted, especially a cyclic or fused cyclic ring and includes a mono-, bi-, or tricyclic, carbo- or heterocyclic ring, wherein the ring is either unsubstituted or substituted in one to five position(s) with halo, haloalkyl, hydroxyl, nitro, trifluoromethyl, $C_1$–$C_6$ straight or branched chain alkyl, $C_2$–$C_6$ straight or branched chain alkenyl, $C_1$–$C_6$ alkoxy, $C_2$–$C_6$ alkenyloxy, phenoxy, benzyloxy, amino, thiocarbonyl, ester, thioester, cyano, imino, alkylamino, aminoalkyl, sulfhydryl, thioalkyl, and sulfonyl; wherein the individual ring sizes are 5–8 members; wherein the heterocyclic ring contains 1–4 heteroatom(s) selected from the group consisting of O, N, or S; wherein aromatic or tertiary alkyl amines are optionally oxidized to a corresponding N-oxide. Particularly preferred aryl or heteroaryl moieties include but are not limited to phenyl, benzyl, naphthyl, pyrrolyl, pyrrolidinyl, pyridinyl, pyrimidinyl, purinyl, quinolinyl, isoquinolinyl, furyl, thiophenyl, imidazolyl, oxazolyl, thiazolyl, pyrazolyl, and thienyl.

"Phenyl" includes all possible isomeric phenyl radicals, optionally monosubstituted or multi-substituted with substituents selected from the group consisting of amino, trifluoromethyl, $C_1$–$C_6$ straight or branched chain alkyl, $C_2$–$C_6$ straight or branched chain alkenyl, carbonyl, thiocarbonyl, ester, thioester, alkoxy, alkenoxy, cyano, nitro, imino, alkylamino, aminoalkyl, sulfhydryl, thioalkyl, sulfonyl, hydroxy, halo, haloalkyl, $NR_2$ wherein $R_2$ is selected from the group consisting of hydrogen, ($C_1$–$C_6$)-straight or branched chain alkyl, ($C_3$–$C_6$) straight or branched chain alkenyl or alkynyl, and ($C_1$–$C_4$) bridging alkyl wherein said bridging alkyl forms a heterocyclic ring starting with the nitrogen of $NR_1$ and ending with one of the carbon atoms of said alkyl or alkenyl chain, and wherein said heterocyclic ring is optionally fused to an Ar group.

The term "pharmaceutically acceptable salt, ester, or solvate" refers to salt, ester, or solvates of the subject compounds which possess the desired pharmacological activity and which are neither biologically nor otherwise undesirable. The salt, ester, or solvates can be formed with inorganic acids such as acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, gluconate, glycerophosphate, hemisulfate heptanoate, hexanoate, hydrochloride hydrobromide, hydroiodide, 2-hydroxyethanesulfonate, lactate, maleate, methanesulfonate, naphthylate, 2-naphthalenesulfonate, nicotinate, oxalate, sulfate, thiocyanate, tosylate and undecanoate. Base salt, ester, or solvates include ammonium salts, alkali metal salts such as sodium and potassium salts, alkaline earth metal salts such as calcium and magnesium salts, salt with organic bases such as dicyclohexylamine salts, N-methyl-D-glucamine, and salts with amino acids such as arginine, lysine, and so forth. Also, the basic nitrogen-containing groups can be quarternized with such agents as lower alkyl halides, such as methyl, ethyl, propyl, and butyl chloride, bromides and iodides; dialkyl sulfates like dimethyl, diethyl, dibutyl and diamyl sulfates, long chain halides such as decyl, lauryl, myristyl and stearyl chlorides, bromides and iodides, aralkyl halides like benzyl and phenethyl bromides and others. Water or oil-soluble or dispersible products are thereby obtained.

The compounds of the present invention possess one or more asymmetric center(s) and thus can be produced as mixtures (racemic and non-racemic) of stereoisomers, or as individual enantiomers or diastereomers. The individual stereoisomers may be obtained by using an optically active starting material, by resolving a racemic or non-racemic mixture of an intermediate at some appropriate stage of the synthesis, or by resolution of the compound of formula (I). It is understood that the individual stereoisomers as well as mixtures (racemic and non-racemic) of stereoisomers are encompassed by the scope of the present invention. The S-stereoisomer at atom 1 of formula I is most preferred due to its greater activity.

"Isomers" are different compounds that have the same molecular formula and includes cyclic isomers such as (iso)indole and other isomeric forms of cyclic moieties.

"Stereoisomers" are isomers that differ only in the way the atoms are arranged in space.

"Enantiomers" are a pair of stereoisomers that are non-superimposable mirror images of each other.

"Diastereoisomers" are stereoisomers which are not mirror images of each other.

"Racemic mixture" means a mixture containing equal parts of individual enantiomers. "Non-racemic mixture" is a mixture containing unequal parts of individual enantiomers or stereoisomers.

The term "preventing neurodegeneration" includes the ability to prevent neurodegeneration in patients newly diagnosed as having a neurodegenerative disease, or at risk of developing a new degenerative disease and for preventing further neurodegeneration in patients who are already suffering from or have symptoms of a neurodegenerative disease.

The term "treatment" as used herein covers any treatment of a disease and/or condition in an animal, particularly a human, and includes:

(i) preventing a disease and/or condition from occurring in a subject which may be predisposed to the disease and/or condition but has not yet been diagnosed as having it;

(ii) inhibiting the disease and/or condition, i.e., arresting its development; or (iii) relieving the disease and/or condition, i.e., causing regression of the disease and/or condition.

As used herein, the term "neural tissue damage resulting from ischemia and reperfusion injury" includes neurotoxicity, such as seen in vascular stroke and global and focal ischemia. As used herein, the term "neurodegenerative diseases," includes Alzheimer's disease, Parkinson's disease and Huntington's disease.

The term "ischemia" relates to localized tissue anemia due to obstruction of the inflow of arterial blood. Global ischemia occurs under conditions in which blood flow to the entire brain ceases for a period of time, such as may result from cardiac arrest. Focal ischemia occurs under conditions in which a portion of the brain is deprived of its normal blood supply, such as may result from thromboembolytic occlusion of a cerebral vessel, traumatic head injury, edema, and brain tumors.

The term "cardiovascular disease" relates to myocardial infarction, angina pectoris, vascular or myocardial ischemia, and related conditions as would be known by those of skill in the art which involve dysfunction of or tissue damage to the heart or vasculature, and especially, but not limited to, tissue damage related to PARP activation.

Compounds of the Invention

The PARP inhibitors of the present invention provide impressive protection against vascular stroke damage, as well as against neural or cardiovascular tissue damage. One of the reasons for this superior performance is thought to be that the PARP inhibitors of the invention interfere with more than the NMDA-neurotoxicity and NO-mediated biological pathways.

Preferred PARP inhibitors of the present invention include compounds having formula I:

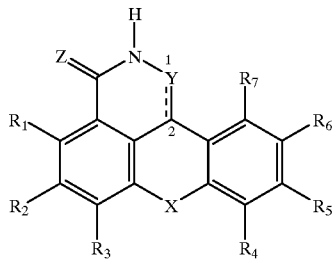

or a pharmaceutically acceptable salt, hydrate, prodrug, or a mixture thereof, wherein Y is alkylhalo, alkyl-CO-G, COG, a direct bond, C=O, O, $NR_8$, or $CR_8$;

G is $NR_9R_{10}$, $OR_9$, $SR_9$, or $R_9$;

Z is O, S, or $NR_{11}$;

X is $NR_{12}$, O, S, $CR_{12}R_{13}$, or C=O;

$R_1$, $R_2$, $R_3$, $R_4$, $R_5$, $R_6$, $R_7$, $R_8$, $R_9$, $R_{10}$, $R_{11}$, $R_{12}$, or $R_{13}$ are independently:

hydrogen, halo, alkylhalo, hydroxy, $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, $Ar_1$, amino, nitro, nitroso, or carboxy, wherein said alkyl, alkenyl, cycloalkyl, cycloalkenyl, and $Ar_1$ groups are independently unsubstituted or substituted with one or more substituent(s) independently selected from the group consisting of $C_3$–$C_8$ cycloalkyl, $C_5$–$C_7$ cycloalkenyl, halo, hydroxyl, nitro, trifluoromethyl, $C_1$–$C_6$ straight or branched chain alkyl, $C_2$–$C_6$ straight or branched chain alkenyl, $C_1$–$C_4$ alkoxy, $C_2$–$C_4$ alkenyloxy, phenoxy, benzyloxy, and $Ar_2$, and wherein $Ar_1$ and $Ar_2$ are independently 1-naphthyl, 2-naphthyl, 2-indolyl, 3-indolyl, 4-indolyl, 2-furyl, 3-furyl, tetrahydrofuranyl 2-thienyl, 3-thienyl, 4-thienyl, 2-pyridyl, 3-pyridyl, 4-pyridyl, or phenyl, each having one or more substituent(s) independently selected from the group consisting of hydrogen, halo, hydroxyl, nitro, trifluoromethyl, $C_1$–$C_6$ straight or branched chain alkyl, $C_2$–$C_6$ straight or branched chain alkenyl, $C_1$–$C_4$ alkoxy or $C_2$–$C_4$ alkenyloxy, phenoxy, and benzyloxy; and with the proviso that when Y is CH or $CCH_3$ and there is a double bond between $C_1$ and $C_2$, and $R_1$–$R_7$ are H, then X is not O.

Preferred compounds of formula I include those where $R_1$, $R_2$, $R_3$, $R_4$, $R_5$, $R_6$, or $R_7$ is a substituted or unsubstituted aliphatic or carbocyclic groups; where $R_1$, $R_2$, $R_3$, $R_4$, $R_5$, $R_6$, or $R_7$ is a heterocyclic groups; where $R_1$, $R_2$, $R_3$, $R_4$, $R_5$, $R_6$, or $R_7$ is halo, hydroxyl, nitro or trifluoromethyl; and where one of $R_1$, $R_2$, or $R_3$ is $Ar_1$, and where $Ar_1$ is 1-naphthyl, 2-naphthyl, 2-indolyl, 3-indolyl, 4-indolyl, 2-furyl, 3-furyl, tetrahydrofuranyl 2-thienyl, 3-thienyl, 4-thienyl, 2-pyridyl, 3-pyridyl, or 4-pyridyl, or phenyl, each having one to five substituents which are independently selected from the group consisting of hydrogen, halo, hydroxyl, nitro, trifluoromethyl, $C_1$–$C_6$ straight or branched alkyl or alkenyl, $C_3$–$C_4$ alkoxy or $C_1$–$C_4$ alkenyloxy, phenoxy, and benzyloxy.

Other preferred compounds of formula I include those where one of $R_1$, $R_2$, or $R_3$ is $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, or $Ar_1$; where one of $R_1$, $R_2$, or $R_3$ is halo, hydroxyl, nitro, or trifluoromethyl; where one of $R_1$, $R_2$, or $R_3$ is nitro or trifluoromethyl; where one of $R_4$, $R_5$, $R_6$, or $R_7$ is $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, or $Ar_1$; and where one of $R_4$, $R_5$, $R_6$, or $R_7$ is $Ar_1$, and where $Ar_1$ is 1-naphthyl, 2-naphthyl, 2-indolyl, 3-indolyl, 4-indolyl, 2-furyl, 3-furyl, tetrahydrofuranyl 2-thienyl, 3-thienyl, 4-thienyl, 2-pyridyl, 3-pyridyl, or 4-pyridyl, or phenyl, each having one to five substituents which are independently selected from the group consisting of hydrogen, halo, hydroxyl, nitro, trifluoromethyl, $C_1$–$C_6$ straight or branched alkyl or alkenyl, $C_1$–$C_4$ alkoxy or $C_1$–$C_4$ alkenyloxy, phenoxy, and benzyloxy.

Yet other preferred compounds of formula I are those where one of $R_4$, $R_5$, $R_6$, or $R_7$ is halo, hydroxyl, nitro, or trifluoromethyl.

Preferred compounds of formula II include those where $R_1$, $R_2$, $R_3$, $R_4$, $R_5$, $R_6$, or $R_7$ is a substituted or unsubstituted aliphatic or carbocyclic group; where $R_1$, $R_2$, $R_3$, $R_4$, $R_5$, $R_6$, or $R_7$ is a heterocyclic group; where $R_1$, $R_2$, $R_3$, $R_4$, $R_5$, $R_6$, and $R_7$ are hydrogen; where $R_1$, $R_2$, $R_3$, $R_4$, $R_5$, $R_6$, and $R_7$ are halo, hydroxyl, nitro or trifluoromethyl; and where one of $R_1$, $R_2$, or $R_3$ is $Ar_1$, and where $Ar_1$ is 1-naphthyl, 2-naphthyl, 2-indolyl, 3-indolyl, 4-indolyl, 2-furyl, 3-furyl, tetrahydrofuranyl 2-thienyl, 3-thienyl, 4-thienyl, 2-pyridyl, 3-pyridyl, or 4-pyridyl, or phenyl, each having one to five substituents which are independently selected from the group consisting of hydrogen, halo, hydroxyl, nitro, trifluoromethyl, $C_1$–$C_6$ straight or branched alkyl or alkenyl, $C_1$–$C_4$ alkoxy or $C_3$–$C_4$ alkenyloxy, phenoxy, and benzyloxy.

Other preferred compounds of formula II include those where one of $R_1$, $R_2$, or $R_3$ is $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, or $Ar_1$; where one of $R_1$, $R_2$, or $R_3$ is halo, hydroxyl, nitro, or trifluoromethyl; where one of $R_1$, $R_2$, or $R_3$ is nitro or trifluoromethyl; where one of $R_4$, $R_5$, $R_6$, or $R_7$ is $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, or $Ar_1$; and where one of $R_4$, $R_5$, $R_6$, or $R_7$ is $Ar_1$, and where $Ar_1$ is 1-naphthyl, 2-naphthyl, 2-indolyl, 3-indolyl, 4-indolyl, 2-furyl, 3-furyl, tetrahydrofuranyl 2-thienyl, 3-thienyl, 4-thienyl, 2-pyridyl, 3-pyridyl, or 4-pyridyl, or phenyl, each having one to five substituents which are independently selected from the group consisting of hydrogen, halo, hydroxyl, nitro, trifluoromethyl, $C_1$–$C_6$ straight or branched alkyl or alkenyl, $C_1$–$C_4$ alkoxy or $C_1$–$C_4$ alkenyloxy, phenoxy, and benzyloxy.

Yet other preferred compounds of formula II include those where one of $R_4$, $R_5$, $R_6$, or $R_7$ is halo, hydroxyl, nitro, or trifluoromethyl.

Preferred compounds of formula III include those where $R_1$, $R_2$, $R_3$, $R_4$, $R_5$, $R_6$, or $R_7$ is a substituted or unsubstituted aliphatic or carbocyclic group; where $R_1$, $R_2$, $R_3$, $R_4$, $R_5$, $R_6$, or $R_7$ is a heterocyclic group; where $R_1$, $R_2$, $R_3$, $R_4$, $R_5$, $R_6$, and $R_7$ are hydrogen; where $R_1$, $R_2$, $R_3$, $R_4$, $R_5$, $R_6$, and $R_7$ are halo, hydroxyl, nitro or trifluoromethyl; and where one of $R_1$, $R_2$, or $R_3$ is $Ar_1$, and where $Ar_1$ is 1-naphthyl, 2-naphthyl, 2-indolyl, 3-indolyl, 4-indolyl, 2-furyl, 3-furyl, tetrahydrofuranyl 2-thienyl, 3-thienyl, 4-thienyl, 2-pyridyl, 3-pyridyl, or 4-pyridyl, or phenyl, each having one to five substituents which are independently selected from the group consisting of hydrogen, halo, hydroxyl, nitro, trifluoromethyl, $C_1$–$C_6$ straight or branched alkyl or alkenyl, $C_1$–$C_4$ alkoxy or $C_1$–$C_4$ alkenyloxy, phenoxy, and benzyloxy.

Other preferred compounds of formula III include those where one of $R_1$, $R_2$, or $R_3$ is $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, or $Ar_1$; where one of $R_1$, $R_2$, or $R_3$ is halo, hydroxyl, nitro, or trifluoromethyl; where one of $R_1$, $R_2$, or $R_3$ is nitro or trifluoromethyl; where one of $R_4$, $R_5$, $R_6$, or $R_7$ is $C_1$–$C_9$ straight or branched chain alkyl, $C_2$–$C_9$ straight or branched chain alkenyl group, $C_3$–$C_8$ cycloalkyl, $C_5$–$C_9$ cycloalkenyl, or $Ar_1$; and where one of $R_4$, $R_5$, $R_6$, or $R_7$ is $Ar_1$, and where $Ar_1$ is 1-naphthyl, 2-naphthyl, 2-indolyl, 3-indolyl, 4-indolyl, 2-furyl, 3-furyl, tetrahydrofuranyl 2-thienyl, 3-thienyl, 4-thienyl, 2-pyridyl, 3-pyridyl, or 4-pyridyl, or phenyl, each having one to five substituents which are independently selected from the group consisting of hydrogen, halo, hydroxyl, nitro, trifluoromethyl, $C_1$–$C_6$ straight or branched alkyl or alkenyl, $C_1$–$C_4$ alkoxy or $C_1$–$C_4$ alkenyloxy, phenoxy, and benzyloxy.

Yet other preferred compounds of formula III include those where one of $R_4$, $R_5$, $R_6$, or $R_7$ is halo, hydroxyl, nitro, or trifluoromethyl.

Preferred compounds of formula IV include those where $R_1$, $R_2$, $R_3$, $R_4$, $R_5$, $R_6$, or $R_7$ is a substituted or unsubstituted aliphatic or carbocyclic group; where $R_1$, $R_2$, $R_3$, $R_4$, $R_5$, $R_6$, or $R_7$ is a heterocyclic group; where $R_1$, $R_2$, $R_3$, $R_4$, $R_5$, $R_6$, and $R_7$ are hydrogen; where $R_1$, $R_2$, $R_3$, $R_4$, $R_5$, $R_6$, and $R_7$ are halo, hydroxyl, nitro or trifluoromethyl; and where one of $R_1$, $R_2$, or $R_3$ is $Ar_1$, and where $Ar_1$ is 1-naphthyl, 2-naphthyl, 2-indolyl, 3-indolyl, 4-indolyl, 2-furyl, 3-furyl, tetrahydrofuranyl 2-thienyl, 3-thienyl, 4-thienyl, 2-pyridyl, 3-pyridyl, or 4-pyridyl, or phenyl, each having one to five substituents which are independently selected from the group consisting of hydrogen, halo, hydroxyl, nitro, trifluoromethyl, $C_1$–$C_6$ straight or branched alkyl or alkenyl, $C_1$–$C_4$ alkoxy or $C_1$–$C_4$ alkenyloxy, phenoxy, and benzyloxy.

Other preferred compounds of formula IV include those where one of $R_1$, $R_2$, or $R_3$ is $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, or $Ar_1$; where one of $R_1$, $R_2$, or $R_3$ is halo, hydroxyl, nitro, or trifluoromethyl; where one of $R_1$, $R_2$, or $R_3$ is nitro or trifluoromethyl; where one of $R_4$, $R_5$, $R_6$, or $R_7$ is $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, or $Ar_1$; and where one of $R_4$, $R_5$, $R_6$, or $R_7$ is $Ar_1$, and where $Ar_1$ is 1-naphthyl, 2-naphthyl, 2-indolyl, 3-indolyl, 4-indolyl, 2-furyl, 3-furyl, tetrahydrofuranyl 2-thienyl, 3-thienyl, 4-thienyl, 2-pyridyl, 3-pyridyl, or 4-pyridyl, or phenyl, each having one to five substituents which are independently selected from the group consisting of hydrogen, halo, hydroxyl, nitro, trifluoromethyl, $C_1$–$C_6$ straight or branched alkyl or alkenyl, $C_1$–$C_4$ alkoxy or $C_1$–$C_4$ alkenyloxy, phenoxy, and benzyloxy.

Yet other preferred compounds of formula IV include those where one of $R_4$, $R_5$, $R_6$, or $R_7$ is halo, hydroxyl, nitro, or trifluoromethyl.

Preferred compounds of formula V include those where $R_1$, $R_2$, $R_3$, $R_4$, $R_5$, $R_6$, or $R_7$ is a substituted or unsubstituted aliphatic or carbocyclic group; where $R_1$, $R_2$, $R_3$, $R_4$, $R_5$, $R_6$, or $R_7$ is a heterocyclic group; when $R_1$, $R_2$, $R_3$, $R_4$, $R_5$, $R_6$, and $R_7$ are hydrogen; where $R_1$, $R_2$, $R_3$, $R_4$, $R_5$, $R_6$, and $R_7$ are halo, hydroxyl, nitro or trifluoromethyl; and where one of $R_1$, $R_2$, or $R_3$ is $Ar_1$, and where $Ar_1$ is 1-naphthyl, 2-naphthyl, 2-indolyl, 3-indolyl, 4-indolyl, 2-furyl, 3-furyl, tetrahydrofuranyl 2-thienyl, 3-thienyl, 4-thienyl, 2-pyridyl, 3-pyridyl, or 4-pyridyl, or phenyl, each having one to five substituents which are independently selected from the group consisting of hydrogen, halo, hydroxyl, nitro, trifluoromethyl, $C_1$–$C_6$ straight or branched alkyl or alkenyl, $C_1$–$C_4$ alkoxy or $C_1$–$C_4$ alkenyloxy, phenoxy, and benzyloxy.

Other preferred compounds of formula V include those where one of $R_1$, $R_2$, or $R_3$ is $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, or $Ar_1$; where one of $R_1$, $R_2$, or $R_3$ is halo, hydroxyl, nitro, or trifluoromethyl; where one of $R_1$, $R_2$, or $R_3$ is nitro or trifluoromethyl; where one of $R_4$, $R_5$, $R_6$, or $R_7$ is $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, or $Ar_1$; and where one of $R_4$, $R_5$, $R_6$, or $R_7$ is $Ar_1$, and where $Ar_1$ is 1-naphthyl, 2-naphthyl, 2-indolyl, 3-indolyl, 4-indolyl, 2-furyl, 3-furyl, tetrahydrofuranyl 2-thienyl, 3-thienyl, 4-thienyl, 2-pyridyl, 3-pyridyl, or 4-pyridyl, or phenyl, each having one to five substituents which are independently selected from the group consisting of hydrogen, halo, hydroxyl, nitro, trifluoromethyl, $C_1$–$C_6$ straight or branched alkyl or alkenyl, $C_1$–$C_4$ alkoxy or $C_1$–$C_4$ alkenyloxy, phenoxy, and benzyloxy.

Yet other preferred compounds of formula V include those where one of $R_4$, $R_5$, $R_6$, or $R_7$ is halo, hydroxyl, nitro, or trifluoromethyl.

Preferred compounds of formula VI include those where $R_1$, $R_2$, $R_3$, $R_4$, $R_5$, $R_6$, or $R_7$ is a substituted or unsubstituted aliphatic or carbocyclic group; where $R_1$, $R_2$, $R_3$, $R_4$, $R_5$, $R_6$, or $R_7$ is a heterocyclic group; where $R_1$, $R_2$, $R_3$, $R_4$, $R_5$, $R_6$, and $R_7$ are hydrogen; where $R_1$, $R_2$, $R_3$, $R_4$, $R_5$, $R_6$, and $R_7$ are halo, hydroxyl, nitro or trifluoromethyl; and where one of $R_1$, $R_2$, or $R_3$ is $Ar_1$, and where $Ar_1$ is 1-naphthyl, 2-naphthyl, 2-indolyl, 3-indolyl, 4-indolyl, 2-furyl, 3-furyl, tetrahydrofuranyl 2-thienyl, 3-thienyl, 4-thienyl, 2-pyridyl, 3-pyridyl, or 4-pyridyl, or phenyl, each having one to five substituents which are independently selected from the group consisting of hydrogen, halo, hydroxyl, nitro, trifluoromethyl, $C_1$–$C_6$ straight or branched alkyl or alkenyl, $C_1$–$C_4$ alkoxy or $C_1$–$C_4$ alkenyloxy, phenoxy, and benzyloxy.

Other preferred compounds of formula VI include those where one of $R_1$, $R_2$, or $R_3$ is $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, or $Ar_1$; where one of $R_1$, $R_2$, or $R_3$ is halo, hydroxyl, nitro, or trifluoromethyl; where one of $R_1$, $R_2$, or $R_3$ is nitro or trifluoromethyl; where one of $R_4$, $R_5$, $R_6$, or $R_7$ is $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, or $Ar_1$; and where one of $R_4$, $R_5$, $R_6$, or $R_7$ is $Ar_1$, and where $Ar_1$ is 1-naphthyl, 2-naphthyl, 2-indolyl, 3-indolyl, 4-indolyl, 2-furyl, 3-furyl, tetrahydrofuranyl 2-thienyl, 3-thienyl, 4-thienyl, 2-pyridyl, 3-pyridyl, or 4-pyridyl, or phenyl, each having one to five substituents which are independently selected from the group consisting of hydrogen, halo, hydroxyl, nitro, trifluoromethyl, $C_1$–$C_6$ straight or branched alkyl or alkenyl, $C_1$–$C_4$ alkoxy or $C_1$–$C_4$ alkenyloxy, phenoxy, and benzyloxy.

Yet other preferred compounds of formula VI include those where one of $R_4$, $R_5$, $R_6$, or $R_7$ is halo, hydroxyl, nitro, or trifluoromethyl.

Preferred compounds of formula VII include those where $R_1$, $R_2$, $R_3$, $R_4$, $R_5$, $R_6$, or $R_7$ is a substituted or unsubstituted aliphatic or carbocyclic group; where $R_1$, $R_2$, $R_3$, $R_4$, $R_5$, $R_6$, or $R_7$ is a heterocyclic group; where $R_1$, $R_2$, $R_3$, $R_4$, $R_5$, $R_6$, and $R_7$ are hydrogen; where $R_1$, $R_2$, $R_3$, $R_4$, $R_5$, $R_6$, and $R_7$ are halo, hydroxyl, nitro or trifluoromethyl; and where one of $R_1$, $R_2$, or $R_3$ is $Ar_1$, and where $Ar_1$ is 1-naphthyl, 2-naphthyl, 2-indolyl, 3-indolyl, 4-indolyl, 2-furyl, 3-furyl, tetrahydrofuranyl 2-thienyl, 3-thienyl, 4-thienyl, 2-pyridyl, 3-pyridyl, or 4-pyridyl, or phenyl, each having one to five substituents which are independently selected from the group consisting of hydrogen, halo, hydroxyl, nitro, trifluoromethyl, $C_1$–$C_6$ straight or branched alkyl or alkenyl, $C_1$–$C_4$ alkoxy or $C_1$–$C_4$ alkenyloxy, phenoxy, and benzyloxy.

Other preferred compounds of formula VII include those where one of $R_1$, $R_2$, or $R_3$ is $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, or $Ar_1$; where one of $R_1$, $R_2$, or $R_3$ is halo, hydroxyl, nitro, or trifluoromethyl; where one of $R_1$, $R_2$, or $R_3$ is nitro or trifluoromethyl; where one of $R_4$, $R_5$, $R_6$, or $R_7$ is $C_1$–$C_9$ straight or branched chain alkyl, $C_2$–$C_9$ straight or branched chain alkenyl group, $C_3$–$C_8$ cycloalkyl, $C_5$–$C_7$ cycloalkenyl, or $Ar_1$; and where one of $R_4$, $R_5$, $R_6$, or $R_7$ is $Ar_1$, and where $Ar_1$ is 1-naphthyl, 2-naphthyl, 2-indolyl, 3-indolyl, 4-indolyl, 2-furyl, 3-furyl, tetrahydrofuranyl 2-thienyl, 3-thienyl, 4-thienyl, 2-pyridyl, 3-pyridyl, or 4-pyridyl, or phenyl, each having one to five substituents which are independently selected from the group consisting of hydrogen, halo, hydroxyl, nitro, trifluoromethyl, $C_1$–$C_6$ straight or branched alkyl or alkenyl, $C_1$–$C_4$ alkoxy or $C_1$–$C_4$ alkenyloxy, phenoxy, and benzyloxy.

Yet other preferred compounds of formula VII include those where one of $R_4$, $R_5$, $R_6$, or $R_7$ is halo, hydroxyl, nitro, or trifluoromethyl.

Another especially preferred embodiment of the invention is a pharmaceutical composition which comprises:

(i) a therapeutically effective amount of the compound of formula XI; and (ii) a pharmaceutically acceptable carrier.

Appropriate PARP inhibitors may be useful in a free base form, in the form of base salts where possible, and in the form of addition salts, as well as in the free acid form. All these forms are within the scope of the invention. In practice, use of the salt form amounts to use of the base form.

Pharmaceutically acceptable salts within the scope of the invention include those derived from mineral acids, such as hydrochloric acid and sulfuric acid, and those derived from organic acids, such as ethanesulfonic acid, benzenesulfonic acid, p-toluenesulfonic acid, and the like, giving the corresponding hydrochloride, sulfonate, ethanesulfonate, benzenesulfonate, p-toluenesulfonate, and the like, of those derived from the neutral compound.

Examples of suitable inorganic bases for the formation of salts of compounds of the invention include the hydroxides, carbonates, and bicarbonates of ammonia; sodium; lithium; potassium; calcium; magnesium; aluminum; zinc; and the like.

Salts may also be formed with suitable organic bases. Organic bases suitable for the formation of pharmaceutically acceptable base addition salts with compounds of the present invention include those that are non-toxic and strong enough to form such salts. These organic bases and the use thereof are readily understood by those skilled in the art. For purposes of illustration, the class of such organic bases may include mono-, di-, and trialkylamines, such as methylamine, dimethylamine, and triethylamine; mono-, di- or trihydroxyalkylamines, such as mono-, di-, and triethanolamine; amino acids, such as arginine and lysine; guanidine; N-methylglucosamine; N-methylglucamine; L-glutamine; N-methylpiperazine; morpholine; ethylenediamine; N-benzylphenethylamine; (trihydroxymethyl) aminoethane; and the like. See, for example, "Pharmaceutical Salts," *J. Pharm. Sci.*, 66:1, 1–19 (1977).

The acid addition salts of the basic compounds may be prepared either by dissolving the free base of a PARP inhibitor in an aqueous or an aqueous alcohol solution or other suitable solvent containing the appropriate acid or base, and isolating the salt by evaporating the solution. Alternatively, the free base of the PARP inhibitor may be reacted with an acid, as well as reacting the PARP inhibitor having an acid group thereon with a base, such that the reactions are in an organic solvent, in which case the salt separates directly or can be obtained by concentrating the solution.

The compounds of the present invention exhibit pharmacological activity and are, therefore, useful as pharmaceuticals. In particular, the compounds exhibit central nervous and cardiac vesicular system activity.

It is understood that tautomeric forms, when possible, are included in the invention. For example, the tautomeric forms of the following compounds are exemplary:

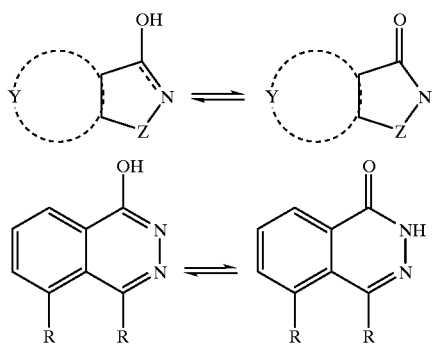

Many of the PARP inhibitors are known and, thus, can be synthesized by known methods from starting materials that are known, may be available commercially, or may be prepared by methods used to prepare corresponding compounds in the literature. See, for example, Suto et al., "Dihydroiso-quinolinones: The Design and Synthesis of a New Series of Potent Inhibitors of Poly(ADP-ribose) Polymerase", *Anticancer Drug Des.*, 6:107–17 (1991), which discloses processes for synthesizing a number of different PARP inhibitors.

Typically, the PARP inhibitors used in the composition of the invention will have an $IC_{50}$ for inhibiting poly(ADP-ribose) synthetase in vitro of 100 μM to 0.08 μM, preferably 50 μM to 0.8 μM, more preferably 30 μM to 0.08 μM, more preferably 10 μM to 0.8 μM, more preferably 50 μM to 10 μM, more preferably 30 μM to 10 μM, more preferably 50 μM to 10 μM, more preferably 30 μM to 5 μM, and even more preferably 40 nM to 0.8 μM. The PARP inhibitor 3,4-dihydro-5-[4-(1-piperidinyl)butoxy]-1(2H)-isoquinolinone, for example, has been reported to inhibit PARP with an $IC_{50}$ of 40 nM by Suto et al., cited above.

Synthesis of PARP Inhibitors

There are multiple routes which may be undertaken to prepare the compounds of the present invention. Two of these routes for the preparation of the xanthene derivatives of this invention are demonstrated below by schemes 1–3 and 4–7.

The xanthene ring may be generically substituted as set forth in formula I. Such xanthene starting derivatives are known in the chemistry literary and are accessible by processes known to one skilled in the art. The process sequence set forth herein does not present an exact sequence of reactions by which the compound must be made; that is, the sequence of reactions can be rearranged in several ways to reach the target molecule.

9-aminomethylxanthenes are available by reduction of 9-carboxamide using sodium boronhydride in dioxane (Scheme 1). Other reduction methods can be employed, using lithium aluminum hydride or other boronhydrides. The solvent can also be varied: DSISO, tetrahydrofuran, diethylether, and other organic solvent can be used. The temperature of the reaction generally is between 0° C. and 200° C.

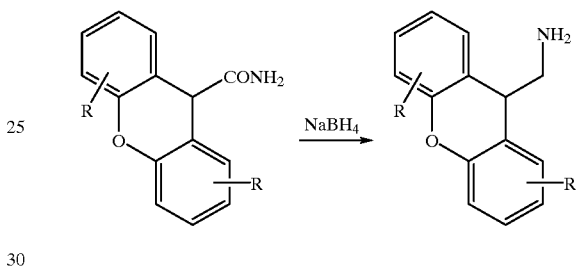

The 9-isocyanomethylxanthene is obtained by condensation of the amino group of the 9-aminomethyl xanthene obtained from Scheme 1 with phosgene in a heated solution of toluene (Scheme 2). Other solvents, such as 1,4-dioxane, chloroform, or p-nitrobenzene, can also be used. The newly formed isocyano functionality serves as an electrophile for the Friedle-Crafts reaction in the next step. Other functionalities including N-carbonylimidazole, N-carbonylbenzotriazole and N-ethylformate can also be applied in this type of reaction. In this case, these functionalities can be formed by reaction of the 9-aminomethylxanthenes with cabonyldiimidazole, carbonyldibenzotriazole and ethyl chloroformate respectively.

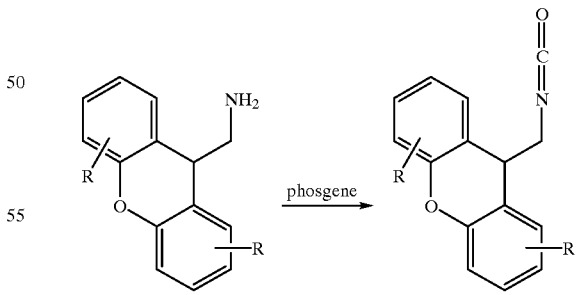

In Scheme 3, the desired xanthene final products can be obtained by an intramolecular Friedle-Crafts acylation using acid as a catalyst. Zinc chloride, aluminum chloride, titanium (IV) chloride, hydrochloric acid, boron trifluoride diethyletherate, or acetic acid may be used, but polyphosphoric acid is often preferred for this type of intramolecular cycloaddition.

Scheme 3

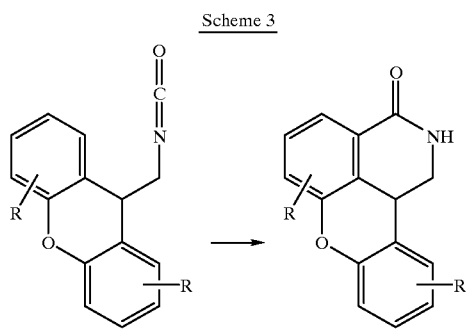

An alternative approach to the preparation of the xanthene derivatives of this invention is illustrated in Schemes 4–7, where the substituent X in Schemes 4–7 can be O, S, or NH.

The starting materials, 3-substituted orthophenyldinitriles or 3-substituted orthophenyldicarboxylic acids, are either readily available or can be prepared by known methods by those skilled in the art. The formation of orthocarbonyl groups from the cyano groups can be achieved by hydrolysis of the aryl nitrile with mineral acids, such as sulphoric acids and hydrochloric acids (Scheme 4). Hydrolysis of the nitrile with sodium hydroxide solution, followed by acidification, can also yield the corresponding acid.

Scheme 4

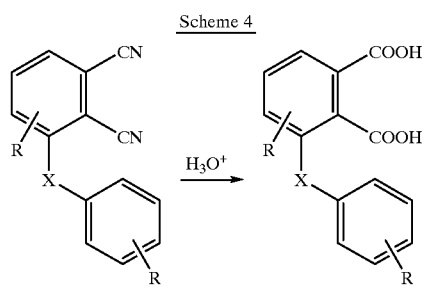

An intramolecular Friedle-Crafts acylation using Lewis acids or polyphosphonic acids as catalysts can provide the xanthene (X=O), acridine (X=NH) or thioxanthene (X=S) skeleton (Scheme 5). This reaction can be run in a regioselective manner determined by R substitutional groups.

Scheme 5

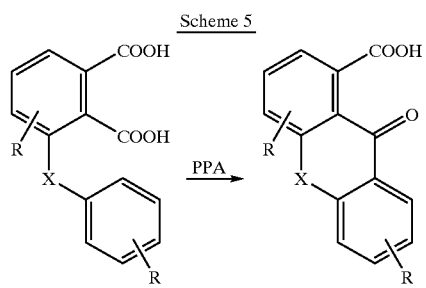

Esterification of the acid of Scheme 5 can be achieved by those skilled in the art through the use of any one of several conventional methods. One of these procedures includes the utilization of diazomethane (Scheme 6). Another similar procedure involves the use of methyl alcohol catalyzed by mineral acids.

Scheme 6

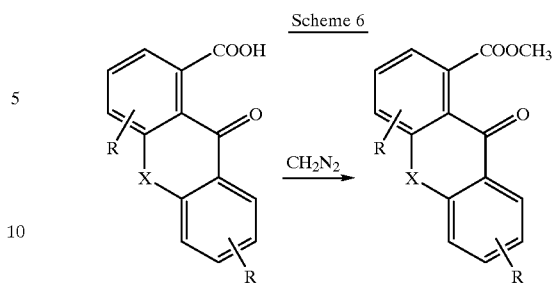

In Scheme 7, the phthalazine ring (Y=NHN=) can be formed by condensation of the ketone ester obtained from Scheme 6 with hydrazine. Hydrogenation of the phthalazine derivative with a catalyst provides the acyl hydrazide (Y=NHNH). Similarly, when the ketone ester reacts with hydroxyamine, the result is a cyclized hydroxymic acid derivative (Y=NH—O). The lactams (Y=NH) can also be made by cycloaddition of the ketone ester with ammonium acetate in acetic acid. Other single amino sources, including ammonia, can be used to replace ammonium acetate.

Scheme 7

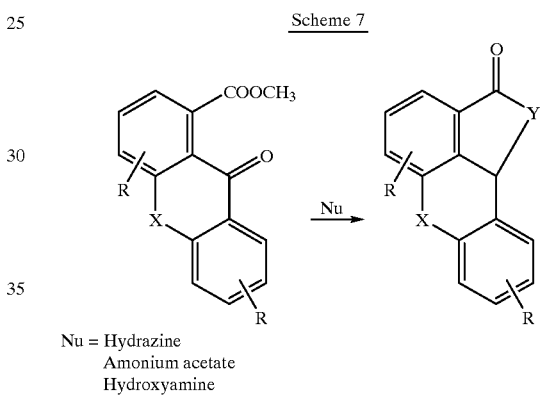

Nu = Hydrazine
Amonium acetate
Hydroxyamine

Methods of Using the Compounds of the Invention

The compounds of the present invention can ameliorate neural or cardiovascular tissue damage, including that following focal ischemia, myocardial infarction, and reperfusion injury. Generally, inhibition of PARP activity spares the cells from energy loss, preventing irreversible depolarization of the neurons, and thus, provides neuroprotection. While not being bound to any one particular theory, it is thought that PARP activation may play a common role in still other excitotoxic mechanisms, perhaps as yet undiscovered, in addition to the production of free radicals and NO.

For the foregoing reasons, the present invention further relates to a method of treating a neurological disorder in an animal, which comprises administering to said animal a therapeutically effective amount of the above-identified compounds.

In a particularly preferred embodiment, the neurological disorder is selected from the group consisting of peripheral neuropathy caused by physical injury or disease state, traumatic brain injury, physical damage to the spinal cord, stroke associated with brain damage, focal ischemia, global ischemia, reperfusion injury, demyelinating disease and neurological disorder relating to neurodegeneration.

Another preferred embodiment is when the reperfusion injury is a vascular stroke.

Yet another preferred embodiment is when the peripheral neuropathy is caused by Guillain-Barre syndrome.

Still another preferred embodiment is when the demyelinating disease is multiple sclerosis.

Another preferred embodiment is when the neurological disorder relating to neurodegeneration is selected from the group consisting of Alzheimer's Disease, Parkinson's Disease, and amyotrophic lateral sclerosis.

An especially preferred embodiment is a method for preventing a neurological disorder in an animal, which comprises administering to said animal a therapeutically effective amount of the above-identified compounds.

A preferred embodiment is when said neurological disorder is selected from the group consisting of peripheral neuropathy caused by physical injury or disease state, traumatic brain injury, physical damage to the spinal cord, stroke associated with brain damage, focal ischemia, global ischemia, and reperfusion injury.

Another preferred embodiment is when the reperfusion injury is a vascular stroke.

Yet another preferred embodiment is when the peripheral neuropathy is caused by Guillain-Barre syndrome.

Still another preferred embodiment is when the demyelinating disease is multiple sclerosis.

Another preferred embodiment is when the neurological disorder relating to neurodegeneration is selected from the group consisting of Alzheimer's Disease, Parkinson's Disease, and amyotrophic lateral sclerosis.

Yet another preferred embodiment is a method of treating a cardiovascular disease in an animal, such as angina pectoris, myocardial infarction, cardiovascular ischemia, and cardiovascular tissue damage related to PARP activation, by administering to said animal an effective amount of the compounds of the present invention.

The present invention also contemplates the use of compound I, II, III, IV, V, VI, VII, VIII, IX, X, or XI for treating a neurological disorder in an animal.

In a particularly preferred embodiment, the neurological disorder is selected from the group consisting of peripheral neuropathy caused by physical injury or disease state, traumatic brain injury, physical damage to the spinal cord, stroke associated with brain damage, focal ischemia, global ischemia, reperfusion injury, demyelinating disease and neurological disorder relating to neurodegeneration.

Another preferred embodiment is when the reperfusion injury is a vascular stroke.

Yet another preferred embodiment is when the peripheral neuropathy is caused by Guillain-Barre syndrome.

Still another preferred embodiment is when the demyelinating disease is multiple sclerosis.

Another preferred embodiment is when the neurological disorder relating to neurodegeneration is selected from the group consisting of Alzheimer's Disease, Parkinson's Disease, and amyotrophic lateral sclerosis.

The present invention also contemplates the use of compound I, II, III, IV, V, VI, VII, VIII, IX, X, or XI in the preparation of a medicament for the treatment of a neurological disorder in an animal.

In a particularly preferred embodiment, the neurological disorder is selected from the group consisting of peripheral neuropathy caused by physical injury or disease state, traumatic brain injury, physical damage to the spinal cord, stroke associated with brain damage, focal ischemia, global ischemia, reperfusion injury, demyelinating disease and neurological disorder relating to neurodegeneration.

Another preferred embodiment is when the reperfusion injury is a vascular stroke.

Yet another preferred embodiment is when the peripheral neuropathy is caused by Guillain-Barre syndrome.

Still another preferred embodiment is when the demyelinating disease is multiple sclerosis.

Another preferred embodiment is when the neurological disorder relating to neurodegeneration is selected from the group consisting of Alzheimer's Disease, Parkinson's Disease, and amyotrophic lateral sclerosis.

Pharmaceutical Compositions of the Invention

The present invention also relates to a pharmaceutical composition comprising:
(i) a therapeutically effective amount of the compound of formula I, II, III, IV, V, VI, VII, VIII, IX, X, or XI, and
(ii) a pharmaceutically acceptable carrier.

An especially preferred embodiment of the invention is a pharmaceutical composition which comprises:
(i) a therapeutically effective amount of a compound of formula I; and
(ii) a pharmaceutically acceptable carrier.

Another especially preferred embodiment of the invention is a pharmaceutical composition which comprises:
(i) a therapeutically effective amount of a compound of formula II; and
(ii) a pharmaceutically acceptable carrier.

Another especially preferred embodiment of the invention is a pharmaceutical composition which comprises:
(i) a therapeutically effective amount of a compound of formula III; and
(ii) a pharmaceutically acceptable carrier.

Another especially preferred embodiment of the invention is a pharmaceutical composition which comprises:
(i) a therapeutically effective amount of a compound of formula IV; and
(ii) a pharmaceutically acceptable carrier.

Yet another especially preferred embodiment of the invention is a pharmaceutical composition which comprises:
(i) a therapeutically effective amount of a compound of formula V; and
(ii) a pharmaceutically acceptable carrier.

Yet another especially preferred embodiment of the invention is a pharmaceutical composition which comprises:
(i) a therapeutically effective amount of a compound of formula VI; and
(ii) a pharmaceutically acceptable carrier.

Another especially preferred embodiment of the invention is a pharmaceutical composition which comprises:
(i) a therapeutically effective amount of a compound of formula VII; and
(ii) a pharmaceutically acceptable carrier.

Another especially preferred embodiment of the invention is a pharmaceutical composition which comprises:
(i) a therapeutically effective amount of the compound of formula VIII; and
(ii) a pharmaceutically acceptable carrier.

Yet another preferred embodiment of the invention is a pharmaceutical composition which comprises:
(i) a therapeutically effective amount of the compound of formula IX; and
(ii) a pharmaceutically acceptable carrier.

Still another preferred embodiment of the invention is a pharmaceutical composition which comprises:

(i) a therapeutically effective amount of the compound of formula X; and (ii) a pharmaceutically acceptable carrier.

The above discussion relating to the preferred embodiments' utility and administration of the compounds of the present invention also applies to the pharmaceutical composition of the present invention.

The term "pharmaceutically acceptable carrier" as used herein refers to any carrier, diluent, excipient, suspending agent, lubricating agent, adjuvant, vehicle, delivery system, emulsifier, disintegrant, absorbent, preservative, surfactant, colorant, flavorant, or sweetener.

For these purposes, the composition of the invention may be administered orally, parenterally, by inhalation spray, topically, rectally, nasally, bucally, vaginally, intraventricularly, via an implanted reservoir in dosage formulations containing conventional non-toxic pharmaceutically-acceptable carriers, or by any other convenient dosage form. The term parenteral as used herein includes subcutaneous, intravenous, intramuscular, intraperitoneal, intrathecal, intraventricular, intrasternal, and intracranial injection or infusion techniques.

When administered parenterally, the composition will normally be in a unit dosage, sterile injectable form (solution, suspension or emulsion) which is preferably isotonic with the blood of the recipient with a pharmaceutically acceptable carrier. Examples of such sterile injectable forms are sterile injectable aqueous or oleaginous suspensions. These suspensions may be formulated according to techniques known in the art using suitable dispersing or wetting agents and suspending agents. The sterile injectable forms may also be sterile injectable solutions or suspensions in non-toxic parenterally-acceptable diluents or solvents, for example, as solutions in 1,3-butanediol. Among the acceptable vehicles and solvents that may be employed are water, saline, Ringer's solution, dextrose solution, isotonic sodium chloride solution, and Hanks' solution. In addition, sterile, fixed oils are conventionally employed as solvents or suspending mediums. For this purpose, any bland fixed oil may be employed including synthetic mono- or di-glycerides, corn, cottonseed, peanut, and sesame oil. Fatty acids such as ethyl oleate, isopropyl myristate, and oleic acid and its glyceride derivatives, including olive oil and castor oil, especially in their polyoxyethylated versions, are useful in the preparation of injectables. These oil solutions or suspensions may also contain long-chain alcohol diluents or dispersants.

Sterile saline is a preferred carrier, and the compounds are often sufficiently water soluble to be made up as a solution for all foreseeable needs. The carrier may contain minor amounts of additives, such as substances that enhance solubility, isotonicity, and chemical stability, e.g., antioxidants, buffers and preservatives.

Formulations suitable for nasal or buccal administration (such as self-propelling powder dispensing formulations) may comprise about 0.1% to about 5% w/w, for example 1% w/w of active ingredient. The formulations for human medical use of the present invention comprise an active ingredient in association with a pharmaceutically acceptable carrier therefore and optionally other therapeutic ingredient(s).

When administered orally, the composition will usually be formulated into unit dosage forms such as tablets, cachets, powder, granules, beads, chewable lozenges, capsules, liquids, aqueous suspensions or solutions, or similar dosage forms, using conventional equipment and techniques known in the art. Such formulations typically include a solid, semisolid, or liquid carrier. Exemplary carriers include lactose, dextrose, sucrose, sorbitol, mannitol, starches, gum acacia, calcium phosphate, mineral oil, cocoa butter, oil of theobroma, alginates, tragacanth, gelatin, syrup, methyl cellulose, polyoxyethylene sorbitan monolaurate, methyl hydroxybenzoate, propyl hydroxybenzoate, talc, magnesium stearate, and the like.

The composition of the invention is preferably administered as a capsule or tablet containing a single or divided dose of the inhibitor. Preferably, the composition is administered as a sterile solution, suspension, or emulsion, in a single or divided dose. Tablets may contain carriers such as lactose and corn starch, and/or lubricating agents such as magnesium stearate. Capsules may contain diluents including lactose and dried corn starch.

A tablet may be made by compressing or molding the active ingredient optionally with one or more accessory ingredients. Compressed tablets may be prepared by compressing, in a suitable machine, the active ingredient in a free-flowing form such as a powder or granules, optionally mixed with a binder, lubricant, inert diluent, surface active, or dispersing agent. Molded tablets may be made by molding in a suitable machine, a mixture of the powdered active ingredient and a suitable carrier moistened with an inert liquid diluent.

The compounds of this invention may also be administered rectally in the form of suppositories. These compositions can be prepared by mixing the drug with a suitable non-irritating excipient which is solid at room temperature, but liquid at rectal temperature, and, therefore, will melt in the rectum to release the drug. Such materials include cocoa butter, beeswax, and polyethylene glycols.

Compositions and methods of the invention also may utilize controlled release technology. Thus, for example, the inventive compounds may be incorporated into a hydrophobic polymer matrix for controlled release over a period of days. The composition of the invention may then be molded into a solid implant suitable for providing efficacious concentrations of the PARP inhibitors over a prolonged period of time without the need for frequent re-dosing. Such controlled release films are well known to the art. Particularly preferred are transdermal delivery systems. Other examples of polymers commonly employed for this purpose that may be used in the present invention include nondegradable ethylene-vinyl acetate copolymer an degradable lactic acid-glycolic acid copolymers which may be used externally or internally. Certain hydrogels such as poly (hydroxyethylmethacrylate) or poly(vinylalcohol) also may be useful, but for shorter release cycles than the other polymer release systems, such as those mentioned above.

The PARP inhibitors are used in the composition in amounts that are therapeutically effective. Said compositions may be sterilized and/or contain adjuvants, such as preserving, stabilizing, welling, or emulsifying agents, solution promoters, salts for regulating the osmotic pressure, and/or buffers. In addition, they may also contain other therapeutically valuable substances. Said compositions are prepared according to conventional mixing, granulating, or coating methods, and contain about 0.1 to 75%, preferably about 1 to 50%, of the active ingredient.

To be effective therapeutically as central nervous system targets, the compounds of the present invention should readily penetrate the blood-brain barrier when peripherally administered. Compounds which cannot penetrate the blood-brain barrier can be effectively administered by an intraventricular route or other appropriate delivery system suitable for administration to the brain.

Doses of the compounds preferably include pharmaceutical dosage units comprising an efficacious quantity of active compound. By an efficacious quantity is meant a quantity sufficient to inhibit PARP and derive the beneficial effects therefrom through administration of one or more of the pharmaceutical dosage units. Preferably, the dose is sufficient to prevent or reduce the effects of vascular stroke or other neurodegenerative diseases.

For medical use, the amount required of the active ingredient to achieve a therapeutic effect will vary with the particular compound, the route of administration, the mammal under treatment, and the particular disorder or disease being treated. A suitable systematic dose of a compound of the present invention or a pharmacologically acceptable salt thereof for a mammal suffering from, or likely to suffer from, any of condition as described hereinbefore is in the range of about 0.1 mg/kg to about 100 mg/kg of the active ingredient compound, the most preferred dosage being about 1 to about 10 mg/kg.

It is understood, however, that a specific dose level for any particular patient will depend upon a variety of factors including the activity of the specific compound employed, the age, body weight, general health, sex, diet, time of administration, rate of excretion, drug combination, and the severity of the particular disease being treated and form of administration.

It is understood that the ordinarily skilled physician or veterinarian will readily determine and prescribe the effective amount of the compound for prophylactic or therapeutic treatment of the condition for which treatment is administered. In so proceeding, the physician or veterinarian could employ an intravenous bolus followed by an intravenous infusion and repeated administrations, parenterally or orally, as considered appropriate. While it is possible for an active ingredient to be administered alone, it is preferable to present it as a formulation.

When preparing dosage form incorporating the compositions of the invention, the compounds may also be blended with conventional excipients such as binders, including gelatin, pregelatinized starch, and the like; lubricants, such as hydrogenated vegetable oil, stearic acid, and the like; diluents, such as lactose, mannose, and sucrose; disintegrants, such as carboxymethylcellulose and sodium starch glycolate; suspending agents, such as povidone, polyvinyl alcohol, and the like; absorbants, such as silicon dioxide; preservatives, such as methylparaben, propylparaben, and sodium benzoate; surfactants, such as sodium lauryl sulfate, polysorbate 80, and the like; colorants such as F.D.& C. dyes and lakes; flavorants; and sweeteners.

The present invention relates to the use of compounds I, II, III, IV, V, VI, VII, VIII, IX, X, or XI in the preparation of a medicament for the treatment of a neurological disorder in an animal.

PARP Assay

A convenient method to determine $IC_{50}$ of a PARP inhibitor compound is a PARP assay using purified recombinant human PARP from Trevigan (Gaithersburg, Md.), as follows: The PARP enzyme assay is set up on ice in a volume of 100 microliters consisting of 100 mM Tris-HCl (pH 8.0), 1 mM $MgCl_2$, 28 mM KCl, 28 mM NaCl, 0.1 mg/ml of herring sperm DNA (activated as a 1 mg/ml stock for 10 minutes in a 0.15% hydrogen peroxide solution), 3.0 micromolar [3H]nicotinamide adenine dinucleotide (470 mci/mmole), 7 micrograms/ml PARP enzyme, and various concentrations of the compounds to be tested. The reaction is initiated by incubating the mixture at 25° C. After 15 minutes of incubation, the reaction is terminated by adding 500 microliters of ice cold 20% (w/v) trichloroacetic acid. The precipitate formed is transferred onto a glass fiber filter (Packard Unifilter-GF/B) and washed three times with ethanol. After the filter is dried, the radioactivity is determined by scintillation counting. The compounds of this invention were found to have potent enzymatic activity in the range of a few NM to 20 M in $IC_{50}$ in this inhibition assay.

Focal cerebral ischemia experiments were performed using male Wistar rats weighing 250–300 g which were anesthetized with 4% halothane. This anesthesia was maintained with 1.0–1.5% halothane until the end of the surgery. The animals were placed in a warm environment to avoid a decrease of body temperature during surgery. An anterior midline cervical incision was made. The right common carotid artery (CCA) was exposed and was isolated from the vagus nerve. A silk suture was placed and tied around the CCA in proximity to the heart. The external carotid artery (ECA) was then exposed and was ligated with a silk suture. A puncture was made in the CCA and a small catheter (PE 10, Ulrich & Co., St-Gallen, Switzerland) was gently advanced to the lumen of the internal carotid artery (ICA). The pterygopalatine artery was not occluded. The catheter was tied in place with a silk suture. Then, a 4-0 nylon suture (Braun Medical, Crissier, Switzerland) was introduced into the catheter lumen and was pushed until the tip blocked the anterior cerebral artery. The length of catheter advanced into the ICA was approximately 19 mm from the origin of the ECA. The suture was maintained in this position by occlusion of the catheter by heat. One cm of catheter and nylon suture were left protruding so that the suture could be withdrawn to allow reperfusion. The skin incision was then closed with wound clips and the animals maintained in a warm environment during recovery from anesthesia. Two hours later, the animals were re-anesthized, the clips were discarded and the wound re-opened. The catheter was cut and the suture was pulled out. The catheter was then obturated again by heat, and wound clips were placed on the wound. The animals were allowed to survive for 24 hours with free access to food and water. The rats were sacrificed with $CO_2$ and were decapitated. The brains were immediately removed, frozen on dry ice and stored at −80° C. The brains were then cut in 0.02 mm-thick sections in a cryocut at −19° C., taking one of every 20 sections. The sections were stained with cresyl violet according to the Nissl procedure. Each section was examined under a light microscope and the regional infarct area was determined according to the presence of cells with morphological changes. Various doses of compounds were tested in this model. The compounds were given in either single or multiple doses, i.p. or i.v., at different times before or after the onset of ischemia. Compounds of this invention were found to have protection in the range of 20 to 80 per cent in this assay.

The experiments of the heart ischemia/reperfusion injury model were performed using female Sprague-Dawley rats weighing 300–350 g which were anesthetized with intraperitoneal ketamine at a dose of 150 mg/kg. The rats were endotracheally incubated and ventilated with oxygen-enriched room air using a Harvard rodent ventilator. Polyethylene catheters inserted into the carotid artery and the femoral vein were used for artery blood pressure monitoring and fluid administration, respectively. Arterial $pCO_2$ was maintained between 35 and 45 mmHg by adjusting the respiratory rate. The rat chests were opened by median sternotomy, the pericardium was incised, and the hearts were cradled with a latex membrane tent. Hemodynamic data were obtained at baseline after at least 15 minute stabilization from the end of the surgical operation. The LAD (left anterior descending) coronary artery was ligated for 40 minutes and was followed by 120 minutes of reperfusion. After 120 minutes of reperfusion, the LAD artery was reoccluded, and a 0.1 ml bolus of monastral blue dye was injected into the left atrium to determine the ischemic risk region. The hearts were then arrested with potassium chloride. The hearts were cut into five 2–3 mm thick transverse slices, and each slice was weighed. The sections were incubated in a 1% solution of triphenyltetrazolium chloride to visualize the infarcted myocardium located within the risk region. Infarct size was calculated by summing the values for each left ventricular slice and expressed as a fraction of the risk region of the left ventricle. Various doses of compounds were tested in this model. The compounds were given in either single or multiple doses, i.p or i.v., at different times before or after the onset of ischemia. The compounds of this invention were found to have ischemia/reperfusion injury protection in the range of 10 to 40 percent in this assay.

As a result of their demonstrated PARP inhibition, the compounds of this invention protect against ischemia-induced degeneration of rat hippocampal neurons in vitro and thus may be useful in disorders arising from cerebral ischemia such as stroke, septic shock, or CNS degenerative disorders. They may also be useful in protecting the spinal cord following trauma. As an experimental result of ischemia/reperfusion injury in rats, the present invention is further directed to a method of prophylactic or therapeutic treatment of heart attack, cardiac arrest, cardiac bypass, diabetes, or risk of damage which comprises administering an effective amount of a compound of the present invention for PARP inhibition in unit dosage form.

EXAMPLES

Example 1

Preparation of 9-aminomethylxanthene

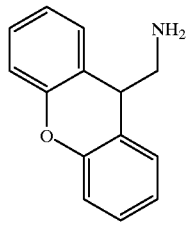

To a stirred suspension of sodium boronhydride (1.89 g, 50 mmol) and 9-xanthencarboxamide (2.25 g, 10 mmol) in dioxane (20 mL) was added acetic acid (3.0 g, 50 mmol) in dioxane (10 mL) over a period of 10 minutes at 10° C.; the reaction mixture was stirred at reflux for 2 hours. The reaction mixture was concentrated to dryness in vacuo, excess reagent was decomposed with water and the solution extracted with chloroform. The extract was washed with water and dried over anhydrous sodium sulphate. The chloroform layer was evaporated in vacuo and the residue was purified by silica gel column chromatography (ethylacetate:methanol, 9:1 as eluent) to give a white solid (1.6 g, 7.6 mmol) in 76.2% yield.

Example 2

Preparation of xanthenyl-9-methylisocyanate

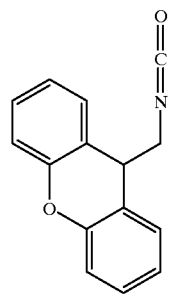

To a stirred solution of 9-aminomethylxanthene (2.11 g, 10 mmol) (see Example 1) in anhydrous 1,4-dioxane (150 mL) was added triphosgene (97.9 mg, 0.33 mmol) at room temperature. The solution was heated at reflux for four hours and then cooled to room temperature. Diethyl ether (200 mL) and water (100 mL) were added to the solution. The organic layer was washed with saturated sodium bicarbonate (50 mL), water (2×50 mL) and brine (200 mL). The organic layer collected was dried over sodium sulfate. The solvent was removed to give an oil residue (2.38 g) without further purification for use in the next step.

Example 3

Preparation of [1]1,11b-Dihydrobenzopyrano[4,3,2-de]isoquinolin-3-one

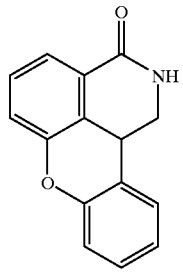

Polyphosphoric acid (12 g) was heated to 90° C. in a 500 mL beaker placed in an oil bath. The xanthenyl-9-methylisocyanate of Example 2 (2.37 g, 10 mmol) was added to the liquid acid portion-wise with manual stirring at 90° C. The mixture was stirred for three minutes and then an additional 100 g of the polyphosphoric acid were added. Vigorous stirring was applied for four minutes while the temperature was kept at 90° C. The mixture was allowed to cool to 60° C. and 40 g crushed ice was added until the polyphosphoric acid was completely hydrolyzed and a brown solid was separated. The solid was collected by vacuum filtration and then recrystallized in chloroform chloride to afford a desired product (1.5 g, 6.33 mmol) in 63% yield.

Example 4

Preparation of 3-phenoxybenzene-1,2-dicarboxylic acid

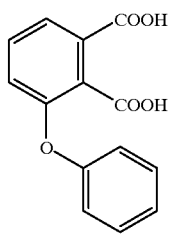

60 g of 75 per cent sulfuric acid was prepared by adding 45 g (24 ml) of concentrated sulfuric acid cautiously, with stirring and cooling, to 15 ml of water. The latter was placed in a 0.5-liter three-necked flask, equipped with a dropping funnel, a mechanical stirrer, and a reflux condenser. The solution was heated in an oil bath to about 120° C., and nitrite (22 g, 100 mmol) was added with stirring during a period of 0.2 hours. The stirring was continued for a further 1 hour while the temperature was maintained at 120° C. The temperature was then allowed to rise to 150° C., and the solution was stirred for another hour. The reaction mixture was cooled and poured into ice-cold water. The precipitated acid was collected by filtration. The crude acid was dissolved in an excess of 10 per cent sodium hydroxide solution, and insoluble material was filtered through a sintered glass funnel while still hot. The filtrate was acidified with dilute sulfuric acid. The solid acid was collected on a Buchner funnel, and dried in the air. The yield of crude acid was (15 g, 78 mmol) 78 per cent.

Example 5

Preparation of 9-oxoxanthene-1-carboxylic acid

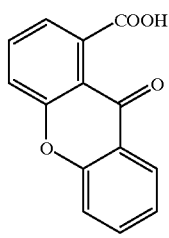

12 g of polyphosphoric acid was heated to 90° C. in a 500 mL beaker placed in an oil bath. The diacid of Example 4 (2.58 g, 10 mmol) was added to the liquid acid portion wise with manual stirring at 100° C. The mixture was stirred for three minutes and then 100 g more of the polyphosphoric acid was added. Vigorous stirring was applied for four minutes while the temperature was kept at 90° C. The mixture was allowed to cool to 60° C. and 40 g of crushed ice was added until the polyphophoric acid was completely hydrolyzed and a yellow oil was separated. The mixture was extracted with three 150 mL portions of methylene chloride and the combined extracts were washed with water, 5 percent aqueous sodium hydroxide solution, and then water until the washings were neutral. The organic layer was dried over magnesium sulfate and the solvent was removed on a rotary evaporator. Purification of this residue on a silica gel column provided the desired product as a solid (1.68 g, 7.0 mmol) in 70% yield.

Example 6

Preparation of 9-oxoxanthene-1-methylcarboxylate

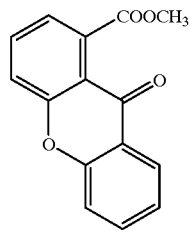

2.14 g of N-methyl-N-nitrosotoluene-p-sulphonamide was dissolved in 30 ml of ether and cooled in ice. A solution of 0.4 g of potassium hydroxide in 10 ml of 96 per cent ethanol was added. If a precipitate forms, add more ethanol until it just dissolves. After 5 minutes, the ethereal diazomethane solution was distilled from a water bath. The ethereal solution contained 0.32–0.35 g of diazomethane. The 9-oxoxanthene-1-carboxylic acid of Example 5 (1.29 g, 5 mmol) was dissolved in absolute methanol, cooled to 0° C., and the ethereal solution of diazomethane was added in a small portion until gas evolution ceased. The solution showed a pale yellow color. The desired ester was obtained by removal of the solvent in vacuum to give a clear oil (1.36 g, 5 mmol) in 100% yield.

Example 7

Preparation of [1]1,2,3,11b-tetrahydrobenzopyrano [4,3,2-de]phthalazin-3-one, and (2H) benzopyrano [4,3,2-de]phthalazin-3-one

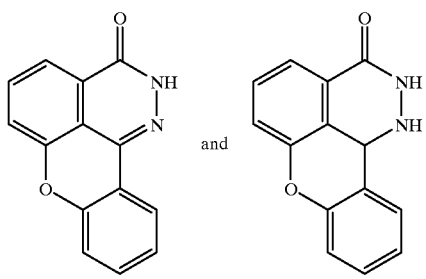

Synthesis of (2H) benzopyrano[4,3,2-de]phthalazin-3-one

To a solution of the ester of Example 6 (1.36 g, 5 mmol) in absolute ethanol (10 mL) was added anhydrous hydrazine in ethanol (1 mL) drop wise at room temperature. The solution was refluxed overnight and cooled to room temperature. Ice-cold water (100 mL) was added and gray solid was separated. The solid was collected by vacuum filtration and washed with water to provide (2H) benzopyrano [4,3,2-de]phthalazin-3-one.

Synthesis of [1]1,2,3,11b-tetrahydrobenzopyrano[4,3,2-de]-phthalazine-3-one

The solid was dissolved in glacial acetic acid (100 mL) and the solution was placed in a hydrogenation bomb. Palladium (10% on carbon, 500 mg) was added. The bomb was set at a pressure of 2000 psi and stirred for 20 hours. The mixture of the content was poured through a fluted filter paper to remove the catalyst. The solvent of the filtrate was removed in vacuo to give a yellow solid which was recrystallized in chloroform to afford the desired product (0.95 g, 4.0 mmol) in 80% yield.

Example 8

Preparation of [1]1,10b dihydrobenzopyrano[4,3,2-de]isoindolin-1-one

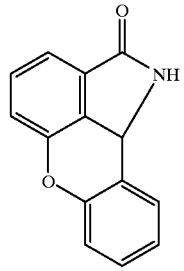

A mixture of ammonium acetate (115 mg, 1.5 mmol), glacial acetic acid (1.5 mL) and the 9-oxoxanthene-1-methylcarboxylate of Example 6 (272 mg, 1.0 mmol) was refluxed for six hours. The solution was placed in a hydrogenation bomb with additional acetic acid (10 mL) added. Palladium (10% on carbon, 100 mg) was added. The bomb was set at a pressure of 2000 psi and stirred for 20 hours. The mixture of the content was poured through a fluted filter paper to remove the catalyst. The solvent of the filtrate was removed in vacuo to give a solid which was recrystallized in chloroform to afford the desired product (66 mg, 0.3 mmol) in 30% yield.

Example 9

Preparation of [2]3,11b-Dihydroxantheno[1,9-de][1,2]oxazin-3-one

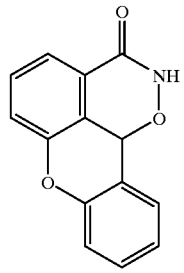

To a solution of the ester of Example 6 (1.36 g, 5 mmol) in absolute ethanol (10 mL) was added anhydrous hydrazine in ethanol (1 mL) drop wise at room temperature. The solution was refluxed overnight and cooled to room temperature. Ice-cold water (100 mL) was added and brown solid was separated. The solid was collected by vacuum filtration and washed with water.

A solution of this crude solid hydroxamic acid in acetic acid (100 mL) was placed in a high pressure bomb, 5 mL of settled Raney nickel catalyst was added, the cap was securely fastened and hydrogen gas was introduced until the pressure was 1000 psi. The mechanical stirring device was set in motion and the reaction was allowed to proceed overnight. The mixture of the content was poured through a fluted filter paper to remove the catalyst (do not permit the catalyst to become dry since it is likely to ignite). Removal of the solvent of the filtrate gave a brown solid which was recrystallized in chloroform to afford the desired product (0.24 g, 1.0 mmol) in 25% yield.

Example 10

Preparation of [1]1,3,11b-Trihydrobenzopyrano[4,3,2-de]isoquinolin-1,3-dione

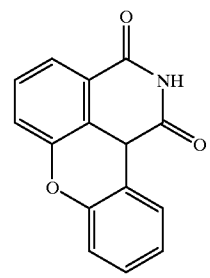

from Example 3.

Example 11

A patient is diagnosed as suffering from a vascular stroke. The patient may then be administered a PARP inhibitor, such as set forth in examples 1 through 10, in the form of a capsule or tablet containing a single or divided dose of the inhibitor. After this initial treatment, the patient may be optionally administered the same or different PARP inhibitor in the form of a capsule or tablet. It would be expected that no further occurrences of the vascular stroke would develop.

Example 12

A patient is diagnosed as suffering from a vascular stroke. The patient may then be administered a PARP inhibitor, such as set forth in examples 1 through 10, in the form of a capsule or tablet containing a single or divided dose of the inhibitor. After this initial treatment, the patient may be optionally administered the same or different PARP inhibitor by direct injection. It would be expected that no further occurrences of the vascular stroke would develop.

Example 13

A patient is diagnosed as suffering from a vascular stroke. The patient may then be administered a PARP inhibitor, such as set forth in examples 1 through 10, in the form of a capsule or tablet containing a single or divided dose of the inhibitor. After this initial treatment, the patient may be optionally administered the same or different PARP inhibitor by intermittent or continuous administration by subdural pump. It would be expected that no further occurrences of the vascular stroke would develop.

Example 14

A patient is diagnosed as suffering from a vascular stroke. The patient may then be administered a PARP inhibitor, such as set forth in examples 1 through 10, in the form of a capsule or tablet containing a single or divided dose of the inhibitor. After this initial treatment, the patient may be optionally administered the same or different PARP inhibitor by intermittent or continuous administration by implantation of a biocompatible, polymeric matrix delivery system. It would be expected that no further occurrences of the vascular stroke would develop.

Example 15

A patient is diagnosed with a disorder requiring the administration of a PARP inhibitor. The patient may then be administered a PARP inhibitor, such as set forth in examples 1 through 10, in the form of a capsule or tablet containing a single or divided dose of the inhibitor. After this initial treatment, the patient may be optionally administered the same or different PARP inhibitor by capsule or tablet, direct injection, subdural pump, or implantation of a biocompatible, polymeric matrix delivery system. It would be expected that the treatment would alleviate the disorder, either in part or in its entirety and that no further occurrences of the disorder would develop.

Example 16

A treatment such as that described in Example 15 wherein the patient is diagnosed with a peripheral neuropathy caused by physical injury.

Example 17

A treatment such as that described in Example 15 wherein the patient is diagnosed with a peripheral neuropathy caused by disease state.

Example 18

A treatment such as that described in Example 15 wherein the patient is diagnosed with Guillain-Barre syndrome.

Example 19

A treatment such as that described in Example 15 wherein the patient is diagnosed with traumatic brain injury.

Example 20

A treatment such as that described in Example 15 wherein the patient is diagnosed with physical damage to the spinal cord.

Example 21

A treatment such as that described in Example 15 wherein the patient is diagnosed with stroke associated with brain damage.

Example 22

A treatment such as that described in Example 15 wherein the patient is diagnosed with focal ischemia.

Example 23

A treatment such as that described in Example 15 wherein the patient is diagnosed with global ischemia.

Example 24

A treatment such as that described in Example 15 wherein the patient is diagnosed with reperfusion injury.

Example 25

A treatment such as that described in Example 15 wherein the patient is diagnosed with a demyelinating disease.

Example 26

A treatment such as that described in Example 15 wherein the patient is diagnosed with multiple sclerosis.

Example 27

A treatment such as that described in Example 15 wherein the patient is diagnosed with a neurological disorder relating to neurodegeneration.

Example 28

A treatment such as that described in Example 15 wherein the patient is diagnosed with Alzheimer's Disease.

Example 29

A treatment such as that described in Example 15 wherein the patient is diagnosed with Parkinson's Disease.

Example 30

A treatment such as that described in Example 15 wherein the patient is diagnosed with amyotrophic lateral sclerosis.

Example 31

A treatment such as that described in Example 15 wherein the patient is diagnosed with a cardiovascular disease.

Example 32

A treatment such as that described in Example 15 wherein the patient is diagnosed with angina pectoris.

Example 33

A treatment such as that described in Example 15 wherein the patient is diagnosed with myocardial infarction.

Example 34

A treatment such as that described in Example 15 wherein the patient is diagnosed with cardiovascular tissue damage related to PARP activation.

The invention being thus described, it will be obvious that the same may be varied in many ways. Such variations are not to be regarded as a departure from the spirit and scope of the invention, and all such modifications are intended to be included within the scope of the following claims.

What is claimed is:

1. The compound of the formula:

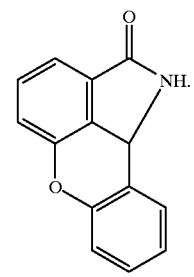

2. A pharmaceutical composition which comprises:
   (i) a therapeutically effective amount of the compound of claim 1; and
   (ii) a pharmaceutically acceptable carrier.
3. A method of treating a neurological disorder in an animal, comprising administering to said animal a therapeutically effective amount of the compound of claim 1.

4. The method of claim 3, wherein the neurological disorder is selected from the group consisting of peripheral neuropathy caused by physical injury or disease state, traumatic brain injury, physical damage to the spinal cord, stroke associated with brain damage, focal ischemia, global ischemia, reperfusion injury, demyelinating disease and neurological disorder relating to neurodegeneration.

5. The method of claim 4, wherein the reperfusion injury is vascular stroke.

6. The method of claim 4, wherein the peripheral neuropathy is caused by Guillain-Barre syndrome.

7. The method of claim 4, wherein the demyelinating disease is multiple sclerosis.

8. The method of claim 4, wherein the neurological disorder relating to neurodegeneration is selected from the group consisting of Alzheimer's Disease, Parkinson's Disease, and amyotrophic lateral sclerosis.

9. A method of treating a cardiovascular disease in an animal, comprising administering to said animal an effective amount of the compound of claim 1.

10. The method of claim 9, wherein the cardiovascular disease is selected from the group consisting of angina pectoris, myocardial infarction, and cardiovascular tissue damage related to PARP activation.

* * * * *